(12) United States Patent
Dessain et al.

(10) Patent No.: US 8,999,707 B2
(45) Date of Patent: Apr. 7, 2015

(54) METHOD OF MAKING HYBRID CELLS THAT EXPRESS USEFUL ANTIBODIES

(75) Inventors: Scott K. Dessain, Wynnewood, PA (US); Sharad P. Adekar, Secane, PA (US)

(73) Assignee: Thomas Jefferson University, Philadelphia, PA (US)

( * ) Notice: Subject to any disclaimer, the term of this patent is extended or adjusted under 35 U.S.C. 154(b) by 337 days.

(21) Appl. No.: 12/864,889

(22) PCT Filed: Jan. 28, 2009

(86) PCT No.: PCT/US2009/000562
§ 371 (c)(1),
(2), (4) Date: Sep. 17, 2010

(87) PCT Pub. No.: WO2009/105150
PCT Pub. Date: Aug. 27, 2009

(65) Prior Publication Data
US 2011/0002937 A1 Jan. 6, 2011

Related U.S. Application Data

(60) Provisional application No. 61/062,584, filed on Jan. 28, 2008.

(51) Int. Cl.
| | | |
|---|---|---|
| C12N 5/06 | (2006.01) | |
| C12N 5/00 | (2006.01) | |
| C07K 16/12 | (2006.01) | |
| C12N 5/16 | (2006.01) | |

(52) U.S. Cl.
CPC ............ *C07K 16/1282* (2013.01); *C12N 5/163* (2013.01); *C07K 2316/96* (2013.01); *C07K 2317/21* (2013.01); *C07K 2317/56* (2013.01); *C07K 2317/92* (2013.01); *C12N 2501/23* (2013.01); *C12N 2501/52* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 6,541,225 B1 | 4/2003 | Li | 435/69.6 |
| 7,491,530 B2* | 2/2009 | Dessain et al. | 435/325 |
| 2003/0224490 A1 | 12/2003 | Dessain et al. | 435/70.21 |
| 2006/0057123 A1 | 3/2006 | Ettinger et al. | 424/93.7 |
| 2011/0008344 A1* | 1/2011 | Dessain et al. | 424/135.1 |

FOREIGN PATENT DOCUMENTS

| | | | |
|---|---|---|---|
| EP | 0508472 A2 | 10/1992 | ............... C12N 5/12 |
| WO | WO 2007/049152 A2 | 5/2007 | |
| WO | 2007063415 A2 | 6/2007 | |

OTHER PUBLICATIONS

Adekar et al., Human Antibodies, 2008, v.17 pp. 33-38.*
Racanelli et al J of Virology, 2006, v.80 p. 3923-3934.*
Arpin et al., "Generation of memory B cells and plasma cells in vitro," *Science* 268 (5211):720-722 (1995).
Casali et al., "Human monoclonals from antigen-specific selection of B lymphocytes and transformation by EBV," *Science* 234 (4775):476-479 (1986).
Cerutti et al., "CD40 ligand and appropriate cytokines induce switching to IgG, IgA, and IgE and coordinated germinal center and plasmacytoid phenotypic differentiation in a human monoclonal IgM+IgD+ B cell line," *J. Immunol.* 160 (5), 2145-2157 (1998).
Crotty et al., "Tracking human antigen-specific memory B cells: a sensitive and generalized ELISPOT system", *J. Immunol. Methods* 286(1-2):111-122 (2004).
Darveau et al., "Efficient preparation of human monoclonal antibody-secreting heterohybridomas using peripheral B lymphocytes cultured in the CD40 system," *J Immunol Methods* 159(1-2): 139-143 (1993).
Dessain et al., "High efficiency creation of human monoclonal antibody-producing hybridomas," *J Immunol Methods* 291(1-2): 109-122 (2004).
De Wildt et al., "A new method for the analysis and production of monoclonal antibody fragments originating from single human B cells". *J. Immunol. Methods* 207(1): 61-67 (1997).
Fecteau et al., "CD40 stimulation of human peripheral B lymphocytes: distinct response from naive and memory cells", *J Immunol* 171(9): 4621-4629 (2003).
Fluckiger et al., "Interleukin 10 (IL-10) upregulates functional high affinity IL-2 receptors on normal and leukemic B lymphocytes", *J Exp Med* 178(5): 1473-1481 (1993).
James et al., "Human monoclonal antibody production. Current status and future prospects", *J Immunol Methods* 100(1-2): 5-40 (1987).
Klein et al, "Human immunoglobulin (Ig)M+IgD+ peripheral blood B cells expressing the CD27 cell surface antigen carry somatically mutated variable region genes: CD27 as a general marker for somatically mutated (memory) B cells", *J Exp Med* 188(9): 1679-1689 (1998).
Kwekkeboom et al., "An efficient procedure for the generation of human monoclonal antibodies based on activation of human B lymphocytes by a murine thymoma cell line", *J. Immunol. Methods*, 160(1): 117-127 (1993).
International Preliminary Report on Patentability for PCT/US2009/000562 dated Aug. 12, 2010.
Nonoyama et al., "B cell activation via CD40 is required for specific antibody production by antigen-stimulated human B cells", *J. Exp. Med.* 178(3): 1097-1102 (1993).
Pirofski et al., "Current state of the hybridoma technology," *J Clin Immunol* 10 (6 Suppl): 5S-12S (1990).
Rousset et al., "Interleukin 10 is a potent growth and differentiation factor for activated human B lymphocytes", *Proc Natl Acad Sci USA* 89, 1890-1893 (1992).

(Continued)

*Primary Examiner* — Michail Belyavskyi
(74) *Attorney, Agent, or Firm* — Drinker Biddle & Reath LLP

(57) ABSTRACT

This invention relates to a novel hybridoma strategy that uses CD27+ B cells cultured in vitro to induce IgM to IgG class switch prior to fusion with a fusion partner. Hybridomas resulting from the fusion between CD27+ B cells and a fusion partner cell line and antibodies secreted from the hybridomas are included in the invention.

13 Claims, 7 Drawing Sheets

(56) References Cited

OTHER PUBLICATIONS

Schultze et al., "CD40-activated Human B Cells: An Alternative Source of Highly Efficient Antigen Presenting Cells to Generate Autologous Antigen-Specific T Cells for Adoptive Immunotherapy," *J Clin Invest* 100(11): 2757-2765 (1997).
Shi et al., "Functional analysis of human memory B-cell subpopulations: IgD+CD27+ B cells are crucial in secondary immune response by producing high affinity IgM," *Clin Immunol* 108(2): 128-137 (2003).
Tangye et al., "Identification of functional human splenic memory B cells by expression of CD148 and CD27," *J Exp Med* 188(9): 1691-1703 (1998).
Tangye et al. "A division-linked mechanism for the rapid generation of Ig-secreting cells from human memory B cells," *J Immunol* 170(1): 261-269 (2003).
Thompson et al., "Human monoclonal anti-D secreting heterohybridomas from peripheral B lymphocytes expanded in the CD40 system," *J Immunol Methods* 175(1): 137-140 (1994).
Traggiai et al., "An efficient method to make human monoclonal antibodies from memory B cells: potent neutralization of SARS coronavirus," *Nat Med* 10(8): 871-875 (2004).
Urashima et al., "CD40 ligand triggered interleukin-6 secretion in multiple myeloma," *Blood* 85(7): 1903-1912 (1995).
Werner-Favre et al., "IgG subclass switch capacity is low in switched and in IgM-only, but high in IgD+IgM+, post-germinal center (CD27+) human B cells," *Eur J Immunol* 31(1): 243-249 (2001).
Néron, S., et al., "Differential responses of human B-lymphocyte subpopulations to graded levels of CD40-CD154 interaction," *Immunology* 116:4, pp. 454-463 (Dec. 2005).
Jahn, S., et al., "Establishment of human Ig producing heterohybridomas by fusion of mouse myeloma cells with human lymphocytes derived from peripheral blood, bone marrow, spleen, lymph node, and synovial fluid," *Journal of Immunological Methods* 107:1, pp. 59-66 (Feb. 1988).
Jahn, S., et al., "Development of Specific IgG-Producing Human Hybridomas by Fusions of Lymphocytes from Actively Immunized Persons," *Hybridoma* 8:5, pp. 529-534 (1989).
Hagiwara, H., et al., "Preferential generation of IgG-producing human hybridomas against human tumor cells," *Journal of Immunological Methods*, 135:1-2, pp. 263-271 (Dec. 1990).
Li, J., et al., "Human antibodies for immunotherapy development generated via a human B cell hybridoma technology," *The National Academy of Sciences of the USA*, 103:10, pp. 3557-3562 (Mar. 2006).
Maurer, D., et al., "IgM and IgG but not Cytokine Secretion is Restricted to the $CD27^+$ B Lymphocyte Subset," *Journal of Immunology*, 148:12, pp. 3700-3705 (Jun. 1992).
Kawahara, H., et al., "A new human fusion partner, HK-128, for making human-human hybridomas producing monoclonal IgG antibodies," *Cytotechnology*, 4:2, pp. 139-143 (Jan. 1990).
Adekar, S. P., et al., "Hybridoma populations enriched for affinity-matured human IgGs yield high-affinity antibodies specific for botulinum neurotoxins," *Journal of Immunological Methods*, 333:1-2, pp. 156-166 (Feb. 2008).
Fecteau et al., 2004, Characterization of naïve and memory B cell differentiation toward plasma cells following low CD154 stimulation, in "Immunology 2004, Genomic Issues, Immune System, Activation and Allergy, Collection of Free Papers Presented at the 12th International Congress of Immunology and 4th Annual Conference of FOCIS," Medimond International Proceedings, pp. 303-307.
Hintzen et al., 1903, Regulation of CD27 expression on subsets of mature T-lymphocytes, J Immunol. 151(5): 2426-2435, Abstract only.
Adekar et al., 2008, An optimized hybridoma method for cloning post-germinal center human IgG antibodies (poster abstract), in "HAH2008, Abstracts of the 14th International Conference on Human Antibodies and Hybridomas, Nov. 12-14, 2008, New York City, New York," Hum Antibodies 17(1-2):33-38.
Final Oral & Poster Programs, Conference Program for: 14th International Conference on Human Antibodies and Hybridomas, Nov. 12-14, 2008, pp. 39-43.
Goodman et al., (1980) "Antigen-specific molecules from murine T lymphocutes and T cell hybridomas," Mol Immunol. Jul. 1980;17(7):933-45. Abstract only.
Dessain et al., "Use of a novel hetero-hybridoma method to clone potent, high affinity human antibodies specific for botulinum neurotoxins", 13th International Conference on Human Antibodies and Hybridomas Oct. 30, 2007, Milan, Italy, vol. 16, No. 1-2, p. 28-29.
Tangye et al., J Immunol., Oct. 15, 2002, vol. 169, No. 8, p. 4298-4306.

\* cited by examiner

Mutation status and CDR3 sequence of cloned Ig variable regions

| Clone | $V_H$ gene | CDR3 sequence | CDR3 length | Mutations no. | Mutations % |
|---|---|---|---|---|---|
| *BoNT-immune library* | | | | | |
| B1 | V3-30*03 | AKVYGDYARGGFDI | 14 | 9 | 2.5 |
| B2 | V3-33*04 | ATSTADDAFDV | 11 | 40 | 11.5 |
| B3 | V3-30*04 | ARDRFLHSGSYYNILGNYYYGMDV | 24 | 0 | 0 |
| B4 | V3-7*01 | ARVDPYEYYYGMDV | 14 | 13 | 3.6 |
| B5 | V3-7*01 | ARGYDILTGPDYWYYGMDV | 19 | 19 | 5.1 |
| B6 | V3-23*04 | ARWRGDIVIAARVYYYWGMDV | 21 | 20 | 5.3 |
| B7 | V3-74*02 | ARVVGYYDILTGPDNYYYYYGMDV | 24 | 2 | 0.5 |
| B8 | V4-39*02 | ASGHYDETGYYNGLFAY | 17 | 27 | 7.4 |
| B9 | V4-59*01 | ARQDGRLRFRSQYYYYGMDV | 20 | 4 | 1.1 |
| B10 | V4-39*01 | ARRDIWELANFDY | 13 | 1 | 0.3 |
| B11 | V4-34*01 | VRGRGHDFSSAHYSMEGNDY | 20 | 16 | 4.3 |
| B12 | V4-b*02 | ARGQSTGWFYFDS | 13 | 13 | 3.7 |
| B13 | V4-59*01 | ARHIVAAEGAGLANWFDP | 18 | 35 | 9.5 |
| B14 | V4-59*01 | ARGHATGSYEWLDP | 14 | 34 | 9.5 |
| B15 | V3-74*01 | ARAGELYGDYVLW | 13 | 5 | 1.4 |
| *Vaccinia-immune library* | | | | | |
| V1 | V1-18*01 | ARVGCTNEACYSNHYFYGLDV | 21 | 22 | 5.8 |
| V2 | V1-18*01 | ARDGSGVAARPQSSAWYYGMDV | 22 | 0 | 0 |
| V3 | V3-72*01 | ARVSWGGSYSEAFDI | 15 | 1 | 0.3 |
| V4 | V3-23*01 | AKDSVGYSYGVGWGKQIKDYHYGMDV | 26 | 22 | 5.6 |
| V5 | V3-23*01 | AKALSIAPDEGMDV | 14 | 1 | 0.3 |
| V6 | V4-34*01 | ARGSKWELHY | 10 | 8 | 2.3 |
| V7 | V4-39*01 | VRQDFGDSHLDH | 12 | 27 | 7.7 |
| V8 | V4-31*03 | ARGHSGYVNFDY | 12 | 7 | 2.0 |
| V9 | V4-31*03 | ARGGYYFDY | 9 | 16 | 4.7 |
| V10 | V3-30-3*01 | ATSPSQYYDTSGYYFDSY | 18 | 18 | 4.9 |
| V11 | V4-59*01 | ARTHGEYSSSSAPSLYYYYGMDV | 23 | 16 | 4.2 |
| | | Means (samples B1-V11) | 16.8 | 14.3 | 3.9 |
| *BoNT/A-specific antibodies* | | | | | |
| 1A | V3-20*01 | ARVPATINYYYYGMDV | 18 | 2 | 0.6 |
| 6A | V3-43*02 | AKDVWTYHYDSSGYQYYYGMDV | 24 | 18 | 4.7 |
| 15A | V1-69*11 | ARGLTHGGHSYEASDI | 18 | 47 | 12.9 |
| 31A | V3-23*01 | AKEGAMASLPA | 13 | 32 | 9.2 |
| 30B | V4-59*01 | ARLVRLDSSWFDP | 13 | 42 | 11.9 |

Figure 3

Table 4
Neutralization of BoNT/A *in vivo*

| IgG | Antibody dose, µg | Dosing schedule | Alive/ Tested |
|---|---|---|---|
| 1A | 100 µg | mixed | 0/5 |
| 6A | 100 µg | mixed | 5/5 |
| 15A | 100 µg | mixed | 0/5* |
| 31A | 100 µg | mixed | 0/5 |
| Ctrl | 100 µg | mixed | 0/5 |
| RPMI | | mixed | 0/5 |
| 6A pre | 500 µg | 60 min pre | 3/3 |
| 6A post | 500 µg | 15 min post | 3/3 |
| RPMI | | | 0/6 |

Figure 4

SEQ ID NO: 1
ATGGAGTTTGGGCTGAGCTGGGTTTTCCTTGTTACTATTTTAAAAGG
TGTCCAGTGTGAAGTGCAATTGGTGGAGTCTGGGGGAGGCGTGGT
GAAGCCGGGGGGGTCCCTGAGACTCTCCTGTACAGCTTTTGGATTC
ACGTTTGAGGATTTTGGCATGCACTGGGTCCGTCAAGCTCCAGGGA
AGGGTCTGGAGTGGGTCTCTCTTGTTAGTGGGGAAGGTGGTAGCAA
ATACTATGCCGACTCTGTGAAGGGCCGGTTCACCATCTCCAGAGACA
ACAAGAAGCACTCCCTGTATCTGCACATGAACAGTCTGAAAACTGAG
GACACCGCCTTGTATTACTGTGCAAAAGATGTATGGACCTACCACTA
TGATAGCAGTGGTTACCAATACTACTACGGTATGGACGTCTGGGGC
CAAGGGACCACGGTCACCGTCTCCTCAGCAAGCACCAAAGC

SEQ ID NO: 2
MEFGLSWVFLVTILKGVQCEVQLVESGGGVVKPGGSLRLSCTAFGFTF
EDFGMHWVRQAPGKGLEWVSLVSGEGGSKYYADSVKGRFTISRDNKK
HSLYLHMNSLKTEDTALYYCAKDVWTYHYDSSGYQYYYGMDVWGQGT
TVTVSSASTK

SEQ ID NO: 3
GAAGTGCAATTGGTGGAGTCTGGGGGAGGCGTGGTGAAGCCGGGG
GGGTCCCTGAGACTCTCCTGTACAGCTTTTGGATTCACGTTTGAGGA
TTTTGGCATGCACTGGGTCCGTCAAGCTCCAGGGAAGGGTCTGGAG
TGGGTCTCTCTTGTTAGTGGGGAAGGTGGTAGCAAATACTATGCCGA
CTCTGTGAAGGGCCGGTTCACCATCTCCAGAGACAACAAGAAGCAC
TCCCTGTATCTGCACATGAACAGTCTGAAAACTGAGGACACCGCCTT
GTATTACTGTGCAAAAGATGTATGGACCTACCACTATGATAGCAGTG
GTTACCAATACTACTACGGTATGGACGTCTGGGGC

SEQ ID NO: 4
EVQLVESGGGVVKPGGSLRLSCTAFGFTFEDFGMHWVRQAPGKGLEW
VSLVSGEGGSKYYADSVKGRFTISRDNKKHSLYLHMNSLKTEDTALYYC
AKDVWTYHYDSSGYQYYYGMDVW

Figure 5A

SEQ ID NO: 5
TCAGGAGCCTGCTGTGTCTGTGGCCTTGGGACAGACAGTCAGGATCA
CATGCCAAGGAGACAGCCTCAGAAGCTACTCGGCAAGTTGGTACCAG
CAGAGGCCAGGACAGGCCCCTCTTTTTGTCATGTATGGTAAGGACAA
GCGGCCCTCAGGGATCCCAGACAGATTCTCTGGCTCCGCCTCAGGG
AACACAGCTTCCTTGACCATTACTGGGGCTCAGGCGGAAGATGAGGC
TGACTATTACTGTAACTGCCGGGACAGCAGTAATCAATATTGGATTTT
CGGCGGAGGGACCAAGGTGACCGTCCTAGGTCAGCCCAAGGCTGCC
CCCTCGGTCACTCTGTTCCCGCCCTCCTCTGAGGAGCTTCAAGCCAA
CAAGGCCACACTGGTGTGTCTCATAAGTGACTTCTACCCGGGAGCCG
TGACAGTGGCCTGGAAGGCAGATAGCAGCCCCGTCAAGGCGGGAGT
GGAGACCACCACACCCTCCAAACAAAGCAACAACAAGTACGCGGCCA
GCAGCTATCTGAGCCTGACGCCTGAGCAGTGGAAGTCCCACAGAAG
CTACAGCTGCC

SEQ ID NO: 6
QEPAVSVALGQTVRITCQGDSLRSYSASWYQQRPGQAPLFVMYGKDKR
PSGIPDRFSGSASGNTASLTITGAQAEDEADYYCNCRDSSNQYWIFGGG
TKVTVLGQPKAAPSVTLFPPSSEELQANKATLVCLISDFYPGAVTVAWKA
DSSPVKAGVETTTPSKQSNNKYAASSYLSLTPEQWKSHRSYSC

SEQ ID NO: 7
TCAGGAGCCTGCTGTGTCTGTGGCCTTGGGACAGACAGTCAGGATCA
CATGCCAAGGAGACAGCCTCAGAAGCTACTCGGCAAGTTGGTACCAG
CAGAGGCCAGGACAGGCCCCTCTTTTTGTCATGTATGGTAAGGACAA
GCGGCCCTCAGGGATCCCAGACAGATTCTCTGGCTCCGCCTCAGGG
AACACAGCTTCCTTGACCATTACTGGGGCTCAGGCGGAAGATGAGGC
TGACTATTACTGTAACTGCCGGGACAGCAGTAATCAATATTGGATTTT
C

SEQ ID NO: 8
QEPAVSVALGQTVRITCQGDSLRSYSASWYQQRPGQAPLFVMYGKDKR
PSGIPDRFSGSASGNTASLTITGAQAEDEADYYCNCRDSSNQYWIF

Figure 5B

SEQ ID NO: 9
AGATCTTCTGAGCTGACTCAGGAGCCTGCTGTGTCTGTGGCCTTGGGA
CAGACAGTCAGGATCACATGCCAAGGAGACAGCCTCAGAAGCTACTC
GGCAAGTTGGTACCAGCAGAGGCCAGGACAGGCCCCTCTTTTTGT
CATGTATGGTAAGGACAAGCGGCCCTCAGGGATCCCAGACAGATTCTC
TGGCTCCGCCTCAGGGAACACAGCTTCCTTGACCATTACTGGGGCTCA
GGCGGAAGATGAGGCTGACTATTACTGTAACTGCCGGGACAGCA
GTAATCAATATTGGATTTTCGGCGGAGGGACCAAGGTGACCGTCCTAG
GTGGTGGTGGGGGGTCTGGAGGAGGCTCGAGTGGCGGCGGTGGTTC
GGGAGGCGGAGGCAGCGAAGTGCAATTGGTGGAGTCTGGGGGAGGC
GTGGTGAAGCCGGGGGGGTCCCTGAGACTCTCCTGTACAGCTTTTGG
ATTCACGTTTGAGGATTTTGGCATGCACTGGGTCCGTCAAGCTCCAGG
GAAGGGTCTGGAGTGGGTCTCTCTTGTTAGTGGGGAAGGTGGTAGCA
AATACTATGCCGACTCTGTGAAGGGCCGGTTCACCATCTCCAGAGACA
ACAAGAAGCACTCCCTGTATCTGCACATGAACAGTCTGAAAACTGAGG
ACACCGCCTTGTATTACTGTGCAAAGATGTATGGACCTACC
ACTATGATAGCAGTGGTTACCAATACTACTACGGTATGGACGTCTGGG
GCCAAGGGACCACGGTCACCGTCTCCTGA

SEQ ID NO: 10
RSSELTQDPAVSVALGQTVRITCQGDSLRSYSASWYQQRPGQAPLFVMY
GKDKRPSGIPDRFSGSASGNTASLTITGAQAEDEADYYCNCRDSSNQYWI
FGGGTKVTVLGGGGSGGGSSGGGGSGGGGSEVQLVESGGGVVKPG
GSLRLSCTAFGFTFEDFGMHWVRQAPGKGLEWVSLVSGEGGSKYYADS
VKGRFTISRDNKKHSLYLHMNSLKTEDTALYYCAKDVWTYHYDSSGYQYY
YGMDVWGQGTTVTVS

Figure 5C

SEQUENCE LISTING

<160> NUMBER OF SEQ ID NOS: 10

<210> SEQ ID NO 1
<211> LENGTH: 458
<212> TYPE: DNA
<213> ORGANISM: Homo sapiens

<400> SEQUENCE: 1

```
atggagtttg gctgagctg gttttccctt gttactattt taaaaggtgt ccagtgtgaa      60
gtgcaattgg tggagtctgg gggaggcgtg gtgaagccgg ggggtccct  gagactctcc    120 tgtacagctt ttggattcac gtttgaggat tttggcatgc actgggtccg tcaagctcca    180
gggaagggtc tggagtgggt ctctcttgtt agtggggaag gtggtagcaa atactatgcc    240
```

```
gactctgtga agggccggtt caccatctcc agagacaaca agaagcactc cctgtatctg      300
cacatgaaca gtctgaaaac tgaggacacc gccttgtatt actgtgcaaa agatgtatgg      360
acctaccact atgatagcag tggttaccaa tactactacg gtatggacgt ctggggccaa      420
gggaccacgg tcaccgtctc ctcagcaagc accaaagc                              458
```

```
<210> SEQ ID NO 2
<211> LENGTH: 152
<212> TYPE: PRT
<213> ORGANISM: Homo sapiens

<400> SEQUENCE: 2

Met Glu Phe Gly Leu Ser Trp Val Phe Leu Val Thr Ile Leu Lys Gly
1               5                   10                  15

Val Gln Cys Glu Val Gln Leu Val Glu Ser Gly Gly Gly Val Val Lys
                20                  25                  30

Pro Gly Gly Ser Leu Arg Leu Ser Cys Thr Ala Phe Gly Phe Thr Phe
            35                  40                  45

Glu Asp Phe Gly Met His Trp Val Arg Gln Ala Pro Gly Lys Gly Leu
        50                  55                  60

Glu Trp Val Ser Leu Val Ser Gly Glu Gly Gly Ser Lys Tyr Tyr Ala
65                  70                  75                  80

Asp Ser Val Lys Gly Arg Phe Thr Ile Ser Arg Asp Asn Lys Lys His
                85                  90                  95

Ser Leu Tyr Leu His Met Asn Ser Leu Lys Thr Glu Asp Thr Ala Leu
                100                 105                 110

Tyr Tyr Cys Ala Lys Asp Val Trp Thr Tyr His Tyr Asp Ser Ser Gly
            115                 120                 125

Tyr Gln Tyr Tyr Tyr Gly Met Asp Val Trp Gly Gln Gly Thr Thr Val
        130                 135                 140

Thr Val Ser Ser Ala Ser Thr Lys
145                 150
```

```
<210> SEQ ID NO 3
<211> LENGTH: 360
<212> TYPE: DNA
<213> ORGANISM: Homo sapiens

<400> SEQUENCE: 3
gaagtgcaat tggtggagtc tgggggaggc gtggtgaagc cggggggtc cctgagactc       60 tcctgtacag cttttggatt cacgtttgag gattttggca tgcactgggt ccgtcaagct     120
ccagggaagg gtctggagtg ggtctctctt gttagtgggg aaggtggtag caaatactat     180
gccgactctg tgaagggccg gttcaccatc tccagagaca acaagaagca ctccctgtat     240
ctgcacatga acagtctgaa aactgaggac accgccttgt attactgtgc aaaagatgta     300
tggacctacc actatgatag cagtggttac caatactact acggtatgga cgtctggggc     360
```

```
<210> SEQ ID NO 4
<211> LENGTH: 119
<212> TYPE: PRT
<213> ORGANISM: Homo sapiens

<400> SEQUENCE: 4

Glu Val Gln Leu Val Glu Ser Gly Gly Gly Val Val Lys Pro Gly Gly
1               5                   10                  15

Ser Leu Arg Leu Ser Cys Thr Ala Phe Gly Phe Thr Phe Glu Asp Phe
```

```
              20                  25                  30
Gly Met His Trp Val Arg Gln Ala Pro Gly Lys Gly Leu Glu Trp Val
          35                  40                  45

Ser Leu Val Ser Gly Glu Gly Gly Ser Lys Tyr Tyr Ala Asp Ser Val
 50                  55                  60

Lys Gly Arg Phe Thr Ile Ser Arg Asp Asn Lys Lys Ser His Ser Leu Tyr
 65                  70                  75                  80

Leu His Met Asn Ser Leu Lys Thr Glu Asp Thr Ala Leu Tyr Tyr Cys
                 85                  90                  95

Ala Lys Asp Val Trp Thr Tyr His Tyr Asp Ser Ser Gly Tyr Gln Tyr
                100                 105                 110

Tyr Tyr Gly Met Asp Val Trp
                115

<210> SEQ ID NO 5
<211> LENGTH: 572
<212> TYPE: DNA
<213> ORGANISM: Homo sapiens

<400> SEQUENCE: 5
tcaggagcct gctgtgtctg tggccttggg acagacagtc aggatcacat gccaaggaga     60
cagcctcaga agctactcgg caagttggta ccagcagagg ccaggacagg cccctctttt    120
tgtcatgtat ggtaaggaca gcggccctc agggatccca gacagattct ctggctccgc     180
ctcagggaac acagcttcct tgaccattac tggggctcag gcggaagatg aggctgacta    240
ttactgtaac tgccgggaca gcagtaatca atattggatt tcggcggag ggaccaaggt     300 gaccgtccta ggtcagccca aggctgcccc ctcggtcact ctgttcccgc cctcctctga    360
ggagcttcaa gccaacaagg ccacactggt gtgtctcata agtgacttct acccgggagc    420
cgtgacagtg gcctggaagg cagatagcag ccccgtcaag gcgggagtgg agaccaccac    480
accctccaaa caaagcaaca caagtacgc ggccagcagc tatctgagcc tgacgcctga    540
gcagtggaag tcccacagaa gctacagctg cc                                  572

<210> SEQ ID NO 6
<211> LENGTH: 190
<212> TYPE: PRT
<213> ORGANISM: Homo sapiens

<400> SEQUENCE: 6

Gln Glu Pro Ala Val Ser Val Ala Leu Gly Gln Thr Val Arg Ile Thr
  1               5                  10                  15

Cys Gln Gly Asp Ser Leu Arg Ser Tyr Ser Ala Ser Trp Tyr Gln Gln
                 20                  25                  30

Arg Pro Gly Gln Ala Pro Leu Phe Val Met Tyr Gly Lys Asp Lys Arg
             35                  40                  45

Pro Ser Gly Ile Pro Asp Arg Phe Ser Gly Ser Ala Ser Gly Asn Thr
         50                  55                  60

Ala Ser Leu Thr Ile Thr Gly Ala Gln Ala Glu Asp Glu Ala Asp Tyr
 65                  70                  75                  80

Tyr Cys Asn Cys Arg Asp Ser Ser Asn Gln Tyr Trp Ile Phe Gly Gly
                 85                  90                  95

Gly Thr Lys Val Thr Val Leu Gly Gln Pro Lys Ala Ala Pro Ser Val
            100                 105                 110

Thr Leu Phe Pro Pro Ser Ser Glu Glu Leu Gln Ala Asn Lys Ala Thr
            115                 120                 125
```

Leu Val Cys Leu Ile Ser Asp Phe Tyr Pro Gly Ala Val Thr Val Ala
    130                 135                 140

Trp Lys Ala Asp Ser Ser Pro Val Lys Ala Gly Val Glu Thr Thr Thr
145                 150                 155                 160

Pro Ser Lys Gln Ser Asn Asn Lys Tyr Ala Ala Ser Ser Tyr Leu Ser
                165                 170                 175

Leu Thr Pro Glu Gln Trp Lys Ser His Arg Ser Tyr Ser Cys
            180                 185                 190

<210> SEQ ID NO 7
<211> LENGTH: 283
<212> TYPE: DNA
<213> ORGANISM: Homo sapiens

<400> SEQUENCE: 7
tcaggagcct gctgtgtctg tggccttggg acagacagtc aggatcacat gccaaggaga      60
cagcctcaga agctactcgg caagttggta ccagcagagg ccaggacagg cccctctttt     120
tgtcatgtat ggtaaggaca agcggccctc agggatccca gacagattct ctggctccgc     180
ctcagggaac acagcttcct tgaccattac tggggctcag gcggaagatg aggctgacta     240
ttactgtaac tgccgggaca gcagtaatca atattggatt ttc                       283

<210> SEQ ID NO 8
<211> LENGTH: 94
<212> TYPE: PRT
<213> ORGANISM: Homo sapiens

<400> SEQUENCE: 8

Gln Glu Pro Ala Val Ser Val Ala Leu Gly Gln Thr Val Arg Ile Thr
1               5                   10                  15

Cys Gln Gly Asp Ser Leu Arg Ser Tyr Ser Ala Ser Trp Tyr Gln Gln
                20                  25                  30

Arg Pro Gly Gln Ala Pro Leu Phe Val Met Tyr Gly Lys Asp Lys Arg
            35                  40                  45

Pro Ser Gly Ile Pro Asp Arg Phe Ser Gly Ser Ala Ser Gly Asn Thr
        50                  55                  60

Ala Ser Leu Thr Ile Thr Gly Ala Gln Ala Glu Asp Glu Ala Asp Tyr
65                  70                  75                  80

Tyr Cys Asn Cys Arg Asp Ser Ser Asn Gln Tyr Trp Ile Phe
                85                  90

<210> SEQ ID NO 9
<211> LENGTH: 777
<212> TYPE: DNA
<213> ORGANISM: Homo sapiens

<400> SEQUENCE: 9
agatcttctg agctgactca ggagcctgct gtgtctgtgg ccttgggaca gacagtcagg      60
atcacatgcc aaggagacag cctcagaagc tactcggcaa gttggtacca gcagaggcca     120
ggacaggccc ctcttttttgt catgtatggt aaggacaagc ggccctcagg gatcccagac    180
agattctctg gctccgcctc agggaacaca gcttccttga ccattactgg ggctcaggcg     240
gaagatgagg ctgactatta ctgtaactgc cgggacagca gtaatcaata ttggattttc     300
ggcggaggga ccaaggtgac cgtcctaggt ggtggtgggg gtctggagg aggctcgagt      360 ggcggcggtg gttcgggagg cggaggcagc gaagtgcaat tggtggagtc tgggggaggc     420

```
gtggtgaagc cggggggggtc cctgagactc tcctgtacag cttttggatt cacgtttgag    480
gattttggca tgcactgggt ccgtcaagct ccagggaagg gtctggagtg ggtctctctt    540
gttagtgggg aaggtggtag caaatactat gccgactctg tgaagggccg gttcaccatc    600
tccagagaca caagaagca ctccctgtat ctgcacatga acagtctgaa aactgaggac    660
accgccttgt attactgtgc aaaagatgta tggacctacc actatgatag cagtggttac    720
caatactact acggtatgga cgtctggggc caagggacca cggtcaccgt ctcctga       777
```

<210> SEQ ID NO 10
<211> LENGTH: 258
<212> TYPE: PRT
<213> ORGANISM: Homo sapiens

<400> SEQUENCE: 10

```
Arg Ser Ser Glu Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Ser
            20                  25                  30

Ala Ser Trp Tyr Gln Gln Arg Pro Gly Gln Ala Pro Leu Phe Val Met
        35                  40                  45

Tyr Gly Lys Asp Lys Arg Pro Ser Gly Ile Pro Asp Arg Phe Ser Gly
    50                  55                  60

Ser Ala Ser Gly Asn Thr Ala Ser Leu Thr Ile Thr Gly Ala Gln Ala
65                  70                  75                  80

Glu Asp Glu Ala Asp Tyr Tyr Cys Asn Cys Arg Asp Ser Ser Asn Gln
                85                  90                  95

Tyr Trp Ile Phe Gly Gly Thr Lys Val Thr Val Leu Gly Gly Gly Gly
            100                 105                 110

Gly Gly Ser Gly Gly Gly Ser Ser Gly Gly Gly Ser Gly Gly Gly
            115                 120                 125

Gly Ser Glu Val Gln Leu Val Glu Ser Gly Gly Val Val Lys Pro
    130                 135                 140

Gly Gly Ser Leu Arg Leu Ser Cys Thr Ala Phe Gly Phe Thr Phe Glu
145                 150                 155                 160

Asp Phe Gly Met His Trp Val Arg Gln Ala Pro Gly Lys Gly Leu Glu
                165                 170                 175

Trp Val Ser Leu Val Ser Gly Gly Gly Ser Lys Tyr Tyr Ala Asp
            180                 185                 190

Ser Val Lys Gly Arg Phe Thr Ile Ser Arg Asp Asn Lys Lys His Ser
            195                 200                 205

Leu Tyr Leu His Met Asn Ser Leu Lys Thr Glu Asp Thr Ala Leu Tyr
    210                 215                 220

Tyr Cys Ala Lys Asp Val Trp Thr Tyr His Tyr Asp Ser Ser Gly Tyr
225                 230                 235                 240

Gln Tyr Tyr Tyr Gly Met Asp Val Trp Gly Gln Gly Thr Thr Val Thr
                245                 250                 255

Val Ser
```

METHOD OF MAKING HYBRID CELLS THAT EXPRESS USEFUL ANTIBODIES

REFERENCE TO GOVERNMENT GRANT

This invention was supported in part by grant number R01 AI065967 from the National Institutes of Health. The U.S. Government has certain rights in this invention.

FIELD OF THE INVENTION

The invention relates to the generation of novel hybrid cells (hybridomas) that produce human monoclonal antibodies

BACKGROUND OF THE INVENTION

Many problems associated with antisera were circumvented with the seminal discovery of mouse hybridomas capable of secreting specific monoclonal antibodies (MAbs) against predefined antigens by Kohler and Milstein (Kohler G. and Milstein C., 1975 Nature 256: 495). Since the report of Kohler and Milstein, the production of mouse monoclonal antibodies has become routine.

Monoclonal antibodies are produced by hybrid cells that result from a fusion between normal B-lymphocytes and myeloma cells. The myeloma cell lines used for fusion are B-lymphocyte tumor cell lines that grow well in vitro and can propagate indefinitely, in contrast to normal B-lymphocytes that cannot replicate or produce antibody in vitro for more than a few days. Cells derived from a fusion of the two types of cells combine the in vitro growth characteristics of the myeloma cell line with the production of an antibody derived from the B-lymphocyte.

Hybrid cells (hybridomas) are generally produced from mass fusions between murine splenocytes, which are highly enriched for B-lymphocytes, and myeloma "fusion partner cells" (B. Alberts et al., Molecular Biology of the Cell (Garland Publishing, Inc. 1994); E. Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are called monoclonal antibodies.

Many investigators have attempted to generate human monoclonal antibodies by generating hybridomas with human B-lymphocytes (N. Chiorazzi et al, J. Exp. Med. 156: 930 (1982); C. M. Croce et al., Nature 288:488 (1980); P. A. Edwards et al, Eur. J. Immunol. 12:641 (1982); R. Nowinski et al, Science 210:537 (1980); L. Olsson et al, Proc. Natl. Acad. Sci. USA 77:5429; J. W. Pickering et al, J. Immunol. 129:406 (1982)). Unfortunately, these hybrid cells exhibited poor growth in vitro, low levels of antibody expression, instability of antibody expression, and a poor ability to be cloned by limiting dilution.

Consequently, diverse and cumbersome approaches have been used to produce human monoclonal antibodies. These include "humanizing" mouse antibodies by creating hybrid murine/hybrid immunoglobulin genes and generating antibodies in transgenic mice that bear human immunoglobulin gene loci. However, these methods are only able to produce antibodies that have been generated in mice by the murine immune system. They do not allow the isolation, production, and use of the naturally-occurring antibodies, the immunological memory that the human immune system produces in response to infections and other antigen exposures. The ability to make monoclonal antibodies directly from human B-lymphocytes is therefore needed and would be of considerable value.

Recently, there has been progress in generating human monoclonal antibodies by generating hybridomas using the SP2/0 cell line as a fusion partner. The SP2/0 cell line is an immortal murine myeloma cell line (a malignant B-lineage cell) that expresses an endogenous murine telomerase gene. U.S. Patent Application Publication No. 20030224490 discloses the genetic modification of the SP2/0 cell line to ectopically express interleukin-6 (IL-6) and human telomerase catalytic subunit (hTERT).

However, progress in making fully human monoclonal antibodies has been hampered by the absence of human myelomas suitable for use as fusion partners with the desirable attributes of mouse myeloma cells such as stability, and high antibody production. The use of Epstein-Barr virus (EBV) has proved to be quite efficient for human lymphocyte immortalization (Kozbor D, and Roder J., J. Immunology 1981; 127:1275; Casual O, Science 1986; 234:476), but has certain limitations such as low antibody secretion rate, poor clonogenicity of antibody-secreting lines and frequent loss of antibody expression.

Immortalized human B cells have been employed for monoclonal antibody production. This approach involve the steps of: (a) isolation of peripheral blood lymphocytes enriched in B cells; (b) transformation of the B cells with EBV-viruses or fusion with immortalized human lymphoblastoid cells, and (c) massive screening for the B cell transformants or hybridomas exhibiting the desired antigen-binding specificity. B cell transformation itself is an inefficient process yielding at best 0.1-10% stable transformants. Thus most B cells with the desired specificity are lost in the pool used for subsequent selection process. Whereas researchers have attempted to enrich the population of B cells expressing the desired immunoglobulin by in vitro immunization/activation with the antigen of interest, the activation is again inefficient in the sense that non-specific B cells also proliferate during this process. The identification of specific antibody producing B cells thus largely depends on the final stage of screening, during which tens and thousands of transformed B cell clones are tested for their abilities to bind the antigen. This approach is time consuming and labor intensive.

The production of high-affinity antibodies is dependent on B cells expressing antibodies that have undergone the process of somatic hypermutation, which is the result of a complex set of events that mostly occur within germinal centers (GC). A post-germinal center B cell is a cell that that has undergone somatic hypermutation of its immunoglobulin genes. After completing the germinal center maturation response, B cells can become either memory B-cells, which circulate in the blood and form the foundation of a future immune response against the original antigen, or plasma cells, which home to the bone marrow, terminally differentiate, and secrete immunoglobulins. The development of memory B cells and plasma cells takes place in germinal centers of lymphoid follicles where antigen-driven lymphocytes undergo somatic hypermutation and affinity selection, presumably under the influence of helper T cells.

Typically, to generate hybridomas that secrete human antibodies, human peripheral blood mononuclear cell populations (PBMCs) are fused with a fusion partner cells because human splenic mononuclear cells, which contain ~40% B cells, are not readily available. PBMCs are readily accessible by routine phlebotomy, but contain only about 5% B-cells (Klein et al., 1997 Blood 89: 1288; Dessain et al., 2004 J.

Immunol. Methods 291: 109; Tian et al., 2007 Mol Immunol 44: 2173). However, only about 15% of the B-cells available in peripheral blood express class-switched, post-(GC antibodies (Klein et al., 1997 Blood 89: 1288; Tian et al., 2007 Mol Immunol 44: 2173). Accordingly, fusions with unselected PBMCs commonly yield hybridomas that express IgM antibodies with germline sequences, which are not as desirable as class switched, post-GC antibodies. A disadvantage of prior art methods is the high background of IgM secreting hybridomas. The present invention serves to address the low yield and success rate in generating desirable IgG class switched, post GC antibodies.

Botulism is a life-threatening, flaccid paralysis caused by a neurotoxin produced by the anaerobic bacterium *Clostridium botulinum*. Botulinum neurotoxin poisoning (botulism) arises in a number of contexts including, but not limited to, food poisoning (food borne botulism), infected wounds (wound botulism), and "infant botulism" from ingestion of spores and production of toxin in the intestine of infants. Botulism is a paralytic disease that typically begins with cranial nerve involvement and progresses caudally to involve the extremities. In acute cases, botulism can prove fatal.

Botulinum neurotoxin (BoNT) is found in nature as seven antigenically distinguishable proteins (serotypes A, B, Cl, D, E, F, and G). Botulinum neurotoxin acts at neuromuscular junctions. In addition BoNT has been designated as a category A select bioterrorism agent by the United States Government because of its extreme lethality and its availability from environmental sources (Arnon et al., 2001 JAMA 285: 1059-70; Greenfield and Bronze, 2003 Drug Discov. Today 8:881-8; Marks, 2004 Anesthesiol. Clin. North America 22:509-32). An inhaled lethal dose of BoNT for a 70 kg person is less than 1 microgram; 1 gram contains enough BoNT to kill one million people (Arnon et al., 2001 JAMA 285:1059-70). Thus, devastatingly lethal amounts of BoNT could easily be transported and distributed in secret. Because of the requirement for immediate and prolonged ICU support for exposure victims, a limited civilian exposure could easily overwhelm the intensive care unit capability of a typical American city (NIAID, 2002b).

The chief countermeasures for BoNT exposure have historically been the botulinum toxoid vaccine and therapeutic antibodies. The existing vaccine is an inactivated pentavalent toxoid that induces a potent neutralizing antibody response (Arnon et al., 2001 JAMA 285:1059-70; Gelzleichter et al. 1999 J. Appl. Toxicol. Suppl. 1:S35-8; Siegel, 1998 Immunol. Res. 17:239-51). However, it has not been recommended for use in the general population because the naturally occurring disease is rare and widespread vaccination would render vaccinees resistant to BoNT, which may be required for medical indications such as blepharospasm, dystonia and torticollis (Bell et al., 2000 Pharmacotherapy 20:1079-91). Use of the toxoid vaccine following BoNT exposure is of no value because it is slow to induce a neutralizing antibody response (Arnon et al., 2001 JAMA 285:1059-70).

The effectiveness of therapeutic antibody treatments for BoNT exposure is well established. BoNT-neutralizing immunoglobulin (BoNT-Ig) given prior to BoNT exposure can prevent or eliminate complications (Arnon et al., 2001 JAMA 285:1059-70; Gelzleichter et al. 1999 J. Appl. Toxicol. Suppl. 1:S35-8; Siegel, 1998 Immunol. Res. 17:239-51). BoNT-Ig given after exposure can prevent progression of symptoms, although it cannot reverse synaptic injury that has already occurred. However, the effectiveness of the currently-available BoNT-neutralizing antibodies is limited. Thus, there is a need for additional therapeutic antibodies for BoNT. The present invention satisfies this need.

SUMMARY OF THE INVENTION

The invention provides a method of making a hybridoma. The method comprises culturing CD27+ B cells in the presence of IL-4, IL-10, and CD40L for a period of time in vitro, and fusing the cultured CD27+ B cells with a fusion partner cell line, thereby producing a hybridoma.

In one embodiment, the concentration of IL-4 in the CD27+ B cell culture is about 2 ng/ml. In another embodiment, the concentration of IL-10 in the CD27+ B cell culture is about 10 ng/ml.

In yet another embodiment, CD40L in the CD27+ B cell culture is provided in the form of CD40L displayed on the surface of tCD40L cells during the CD27+ B cell culturing.

In one embodiment, the cultured CD27+ B cells are fused with a fusion partner cell line that ectopically expresses mIL-6 and hTERT to generate a hybridoma.

In another embodiment, the CD27+ B cells are isolated from an immunized subject.

The invention also provides a hybridoma generated from the fusion between cultured CD27+ B cells and a fusion partner cell line, wherein the CD27+ B cells have been cultured in the presence of IL-4, IL-10, and CD40L for a period of time in vitro.

The invention also provides a monoclonal antibody produced by a hybridoma generated from the fusion between cultured CD27+ B cells and a fusion partner cell line, wherein the CD27+ B cells have been cultured in the presence of IL-4, IL-10, and CD40L for a period of time in vitro.

In one embodiment, the invention provides a hybridoma deposited as ATCC accession number PTA-8870.

The invention also provides a method of producing a monoclonal antibody, comprising fusing CD27+ B cells that have been cultured in the presence of IL-4, IL-10, and CD40L for a period of time in vitro with a fusion partner cell line to produce hybridomas; selecting a hybridoma that produces the monoclonal antibody; and culturing the hybridoma to produce the monoclonal antibody.

In one embodiment, the invention provides an antibody produced by fusing CD27+ B cells that have been cultured in the presence of IL-4, IL-10, and CD40L for a period of time in vitro with a fusion partner cell line to produce hybridomas; selecting a hybridoma that produces the monoclonal antibody; and culturing the hybridoma to produce the monoclonal antibody. The invention also provides an antigen-binding fragment of the antibody.

In one embodiment, the antibody binds to an epitope specifically bound by an antibody produced by the hybridoma deposited as ATCC accession number PTA-8870. In another embodiment, the invention provides a monoclonal antibody produced from hybridoma 6A (ATCC accession no. PTA-8870). The antibody provided by said hybridoma may be referenced to herein as "6A". 6A may also be used to refer to said hybridoma.

In another embodiment, the antibody is obtainable from ATCC accession number PTA-8870, or an antibody-binding fragment of said antibody.

The invention also provides an antibody comprising an antibody heavy chain polypeptide comprising an antibody heavy chain variable domain comprising the amino acid sequence SEQ ID NO: 4; and an antibody light chain polypeptide comprising an antibody light chain variable domain comprising the amino acid sequence SEQ ID NO: 8; or an antigen-binding fragment of said antibody.

In one embodiment, the antibody comprises a heavy chain polypeptide comprising the amino acid sequence SEQ ID NO: 2, and a light chain polypeptide comprising the amino acid sequence 6; or an antigen-binding fragment of said antibody.

In yet another embodiment, the invention provides an antibody fragment including but is not limited to a single chain Fv (scFv) fragment, a Fab fragment, a (Fab')$_2$ fragment, and a (scFv')$_2$ fragment. an scFv has been made. sequence information is provided The invention also provides a method of neutralizing BoNT/A in a subject in need thereof, comprising administering to the subject a therapeutically effective amount of an antibody or antigen-binding fragment.

The invention also provides an isolated nucleic acid molecule, wherein the nucleic acid molecule encodes at least one of the antibody heavy chain polypeptide comprising the amino acid sequence SEQ ID NO: 2 or the antibody light chain polypeptide comprising the amino acid sequence SEQ ID NO: 6.

In one embodiment, the isolated nucleic acid molecule comprises a first nucleic acid segment encoding the antibody heavy chain polypeptide and a second nucleic acid segment encoding the antibody light chain polypeptide. In another embodiment, the first nucleic acid segment comprises the nucleotide sequence SEQ ID NO: 1, and the second nucleic acid segment comprises the nucleotide sequence SEQ ID NO: 5.

In another embodiment, the isolated nucleic acid molecule encodes at least one of the antibody heavy chain variable domain comprising the amino acid sequence SEQ ID NO: 4 and the antibody light chain variable domain comprising the amino acid sequence SEQ ID NO: 8.

In another embodiment, the isolated nucleic acid molecule comprises a first nucleic acid segment encoding the antibody heavy chain variable domain and a second nucleic acid segment encoding the antibody light chain variable domain. In yet another embodiment, the first nucleic acid segment comprises the nucleotide sequence 3, and the second nucleic acid segment comprises the nucleotide sequence 7.

ABBREVIATIONS AND SHORT FORMS

The following abbreviations and short forms are used in this specification.

"CD40L" means CD40 ligand.
"BoNT/A" means botulinum neurotoxin serotype A.
"ELISA" means enzyme-linked immunosorbent assay.
"GC" means germinal center.
"huMAb" means human monoclonal antibody.
"Ig" means immunoglobulin.
"Ig H" means immunoglobulin heavy chain.
"Ig L" means immunoglobulin light chain.
"MAb" means monoclonal antibody.
"PCR" means polymerase chain reaction.
"RT-PCR" means reverse transcription PCR.
"scFv" means single chain variable fragment.
"IL" means interleukin.
"hTERT" means human telomerase catalytic subunit.

DEFINITIONS

The definitions used in this application are for illustrative purposes and do not limit the scope of the invention.

The articles "a" and "an" are used herein to refer to one or to more than one (e.g., to at least one) of the grammatical object of the article. By way of example, "an element" means one element or more than one element.

An "antigen" is any agent, e.g., a protein (or immunogenic fragments), a peptide or peptide conjugate, immunogen, vaccine, or a polysaccharide, that elicits an immune response. For example, an immunogenic bolutinum toxin molecule can comprise full length botulinum toxin, or immuogenic fragments thereof. A boultinum vaccine can also be used to elicit an immune response in a animal.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The term "antibody" as used herein refers to an immunoglobulin molecule that contains an antigen binding site which specifically binds an antigen. Structurally, the antibody comprises four polypeptide chains, two heavy (H) chains and two light (L) chains inter-connected by disulfide bonds. The term also encompasses polyclonal and monoclonal antibodies, hybrid, and humanized antibodies.

As used herein, "antigen-binding fragment" with respect to any antibody are fragments of the antibody, such as Fab, F(ab')$_2$, Fv fragments, and single chain variable fragments (scFv), which are capable of binding an epitopic determinant. Antibody fragments can refer to antigen-binding immunoglobulin peptides which are at least about 5 to about 15 amino acids or more in length, and which retain some biological activity or immunological activity of an immunoglobulin. Examples of antigen-binding fragments encompassed within the term "antigen-binding fragments" include but are not limited to (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; (v) an isolated complimentarity determining region (CDR); and (vi) an F(ab')2 fragment, a bivalent fragment comprising two Fab fragments linked by a disulfide bridge at the hinge region. Furthermore, although the two domains of the Fv fragment are generally coded for by separate genes, a synthetic linker can be made that enables them to be made as a single protein chain (known as single chain Fv (scFv); Bird et al. (1988) Science 242:423-426; and Huston et al. (1988) PNAS 85:5879-5883) by recombinant methods. Such single chain antibodies are also encompassed within the term "antigen-binding fragments". Preferred antibody fragments are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations.

As used herein, the term "monoclonal antibody" includes antibodies which display a single binding specificity and affinity for a particular epitope. These antibodies are mammalian-derived antibodies, including murine, human and humanized antibodies. The term "human monoclonal antibody" as used herein, refers to antibodies displaying a single binding specificity which have variable and constant regions derived from human germ-line immunoglobulin sequences.

"Biologically active," as used herein with respect to botulinum neurotoxin neutralizing antibodies, fragments, derivatives, homologs, and analogs means that the antibodies, fragments, derivatives, homologs or analogs have the ability to neutralize a botulinum neurotoxin, as described herein (e.g. BoNT/A).

As used herein, "class switching" or "isotype switching" means a change in the phenotype of an Ig-producing cell. Ig class switching is a critical step in the generation of the diversified biological effector functions of the antibody response. For example, B cells initially produce primarily IgM, a phenotype change into the production of IgG, IgE or IgA is an "isotype switch" or "class switch." Class switching, as used herein, includes two steps: the first step is the provision of trans-spliced transcripts to act as bridging templates for conforming genomic immunoglobulin DNA, and the second step is switch recombination that results in the production of switch circles and rearrangement of genomic Ig DNA to allow production of a different Ig (antibody). In particular, Ig class switching involves DNA recombination between two IgH switch (S) regions through a non-homologous recombination, a process known as class switch recombination (CSR). This process leads to the rearrangement of the S region of the upstream Ig locus to a downstream targeted S region and results in the expression of the downstream isotype. The intervening DNA is looped-out, and excised as the switch circular DNA.

As used herein, an "effective amount" or "therapeutically effective amount" of botulinum neurotoxin neutralizing antibodies, is an amount sufficient to neutralize (mitigate or eliminate) BoNT/A toxin (e.g., reduce or eliminate a symptom of BoNT/A poisoning (botulism)).

The term "expression," as used with respect to a botulinum neurotoxin neutralizing antibody mRNA, refers to transcription of a botulinum neurotoxin neutralizing heavy or light chain nucleic acid sequence, resulting in synthesis of botulinum neurotoxin neutralizing antibody mRNA. "Expression," as used with respect to a botulinum neurotoxin neutralizing antibody, refers to translation of a botulinum neurotoxin neutralizing antibody mRNA, resulting in synthesis of a botulinum neurotoxin neutralizing antibody.

As used herein, the term "fragment" or "segment" as applied to a nucleic acid, refers to a subsequence of a larger nucleic acid. A "fragment" or "segment" of a nucleic acid can be at least about 20 nucleotides in length; for example, at least about 50 nucleotides to about 100 nucleotides; preferably at least about 100 to about 500 nucleotides, more preferably at least about 500 to about 1000 nucleotides, even more preferably at least about 1000 nucleotides to about 1500 nucleotides; particularly, preferably at least about 1500 nucleotides to about 2500 nucleotides; most preferably at least about 2500 nucleotides.

As used herein, the term "fragment" or "segment" as applied to a protein or peptide, refers to a subsequence of a larger protein or peptide. A "fragment" or "segment" of a protein or peptide can be at least about 20 amino acids in length; for example at least about 50 amino acids in length; more preferably at least about 100 amino acids in length, even more preferably at least about 200 amino acids in length, particularly preferably at least about 300 amino acids in length, and most preferably at least about 400 amino acids in length.

As used herein, the term "gene" refers to an element or combination of elements that are capable of being expressed in a cell, either alone or in combination with other elements.

In general, a gene comprises (from the 5' to the 3' end): (1) a promoter region, which includes a 5' nontranslated leader sequence capable of functioning in any cell such as a prokaryotic cell, a virus, or a eukaryotic cell (including transgenic animals); (2) a structural gene or polynucleotide sequence, which codes for the desired protein; and (3) a 3' nontranslated region, which typically causes the termination of transcription and the polyadenylation of the 3' region of the RNA sequence. Each of these elements is operably linked by sequential attachment to the adjacent element. A gene comprising the above elements is inserted by standard recombinant DNA methods into a plant expression vector.

As used herein, "gene products" include any product that is produced in the course of the transcription, reverse-transcription, polymerization, translation, post-translation and/or expression of a gene. Gene products include, but are not limited to, proteins, polypeptides, peptides, peptide fragments, or polynucleotide molecules.

As used herein, "homology" is used synonymously with "identity."

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated' cell is a cell that has been purified from the other cellular components of a tissue. Cells can be isolated by mechanical and/or enzymatic methods. In several embodiments, an isolated population of cells includes greater than about 80%, about 85%, about 90%, about 95%, or greater than about 99% of the cells of interest. In another embodiment, an isolated population of cells is one in which no other cells of a different phenotype can be detected. In a further embodiment, an isolated population of cells is a population of cells that includes less than about 20%, about 15%, about 10%, about 5%, or less than about 1% of a cells of a different phenotype than the cells of interest.

As used herein, the term "library" refers to a polyclonal population of hybridoma cells or to the antibodies secreted by the cells. A library exists in a form that can be screened to identify members of the library (either cells or antibodies) that possess specific characteristics.

The terms "medium", "cell culture medium" and "culture medium" are used interchangeably. The terms refer to the aqueous environment in which eukaryotic or prokaryotic cells are grown in culture. The medium comprises the chemical, nutritional, and hormonal environment. The cell culture medium is "serum-free", when the medium is essentially free of serum from any mammalian source, (e.g. sera from fetal bovine, horse, human, rabbit). By "essentially free" is meant that the cell culture medium comprises between about 0-5% serum, preferably between about 0-1% serum and most preferably between about 0-0.1% serum.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

"Neutralize," as used herein, means to inhibit the biological activity of a botulinum neurotoxin. Preferably, "neutralize," as used herein with respect to a botulinum neurotoxin, means to reduce or inhibit progression of a botulinum neurotoxin exposure in a subject or to reduce or prevent progression in a subject at risk of exposure to a botulinum neurotoxin. Preferred antibodies of this invention act to neutralize (reduce or eliminate) the toxicity of botulinum neurotoxin.

A "nucleic acid" refers to a polynucleotide and includes poly-ribonucleotides and poly-deoxyribonucleotides.

The term "oligonucleotide" typically refers to short polynucleotides of about 50 nucleotides or less in length. It will be understood that when a nucleotide sequence is represented herein by a DNA sequence (e.g., A, T, G, and C), this also includes the corresponding RNA sequence (e.g., a, u, g, c) in which "u" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids which can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptide, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit passive immunity.

"Pharmaceutically acceptable" means physiologically tolerable, for either human or veterinary applications.

As used herein, "pharmaceutical compositions" include formulations for human and veterinary use.

A "preventive" or "prophylactic" treatment is a treatment administered to a subject who does not exhibit signs, or exhibits only early signs, of botulinum neurotoxin exposure or infection of C. botulinum. A prophylactic or preventative treatment is administered for the purpose of decreasing the risk of developing pathology associated with botulinum neurotoxin exposure or infection of C. botulinum.

"Botulinum neurotoxin or C. botulinum-associated disorder," as used herein, refers to a disorder in which there is an association between the presence of botulinum neurotoxin exposure or infection of C. botulinum and clinical signs thereof.

"Botulinum neurotoxin-neutralizing," as used herein with respect to antibodies, refers to an antibody or mixture of antibodies which exhibits the ability to reduce the extent to which a botulinum neurotoxin exposure or infection of C. botulinum elicits a disease/disorder state in an animal. "Botulinum neurotoxin-neutralizing" is used interchangeably with "C. botulinum-neutralizing activity."

A "sample," as used herein, refers to a biological sample from a subject, including normal tissue samples, blood, saliva, feces, or urine. A sample can also be any other source of material obtained from a subject which contains a compound or cells of interest.

As used herein, an antibody "specifically binds," referring to an antibody binding to Botulinum neurotoxin, means that the antibody binds a Botulinum neurotoxin polypeptide, or fragment thereof, but does not bind to a non-Botulinum neurotoxin polypeptide. Antibodies that specifically bind to a Botulinum neurotoxin, or fragment thereof, do not cross-react with antigens outside of the family of Botulinum neurotoxins.

A "subject," as used herein, can be a human or non-human animal. Non-human animals include, for example, livestock and pets, such as ovine, bovine, porcine, canine, feline and murine mammals, as well as reptiles, birds and fish. Preferably, the subject is a human.

"Substantially purified" refers to a peptide or nucleic acid sequence which is substantially homogenous in character due to the removal of other compounds (e.g., other peptides, nucleic acids, carbohydrates, lipids) or other cells originally present. "Substantially purified" is not meant to exclude artificial or synthetic mixtures with other compounds, or the presence of impurities which do not interfere with biological activity, and which may be present, for example, due to incomplete purification, addition of stabilizers, or formulation into a pharmaceutically acceptable preparation.

"Synthetic mutant" includes any purposefully generated mutant or variant protein or nucleic acid. Such mutants can be generated by, for example, chemical mutagenesis, polymerase chain reaction (PCR) based approaches, or primer-based mutagenesis strategies well known to those skilled in the art.

The terms to "treat" or "treatment," as used herein, refer to administering botulinum neurotoxin-neutralizing antibodies or compounds to reduce the frequency with which the effects or symptoms of a botulinum neurotoxin exposure or C. botulinum infection are experienced, to reduce the severity of symptoms, or to prevent effects or symptoms from occurring.

The term "vaccine" as used herein is defined as a material used to provoke an immune response after administration of the material to a mammal. For example, a botulinum neurotoxin vaccine would comprise a molecule derived from botulinum neurotoxin that when administered to a mammal elicits an immune response in the mammal.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and the like.

DESCRIPTION OF THE FIGURES

FIG. 3 is a chart summarizing the mutation status of the CDR3 region of cloned human antibodies. The results indicate that the majority of the antibodies have undergone somatic mutation with a 0.6-12.9% mutation rate.

FIG. 4 is a chart summarizing the ability of the 6A antibody to neutralize BoNT/A in vivo. Each antibody (1A, 6A, 15A, and 31A) was administered on one of three schedules: pre-incubated with BoNT/A for 1 hour prior to injection (mixed); injected 60 minutes prior to the toxin (pre); or injected 15 minutes after the toxin (post). Negative controls included culture medium only (RPMI) and an isotype control IgG (Ctrl). 6A was able to neutralize BoNT/A in vivo in all three scenarios.

FIG. 5, comprising FIGS. 5A through 5C, is a chart depicting the amino acid and nucleic acid sequences of the heavy and light chain domains of the botulinum neurotoxin 6A antibody.

DETAILED DESCRIPTION OF THE INVENTION

Figure 1:
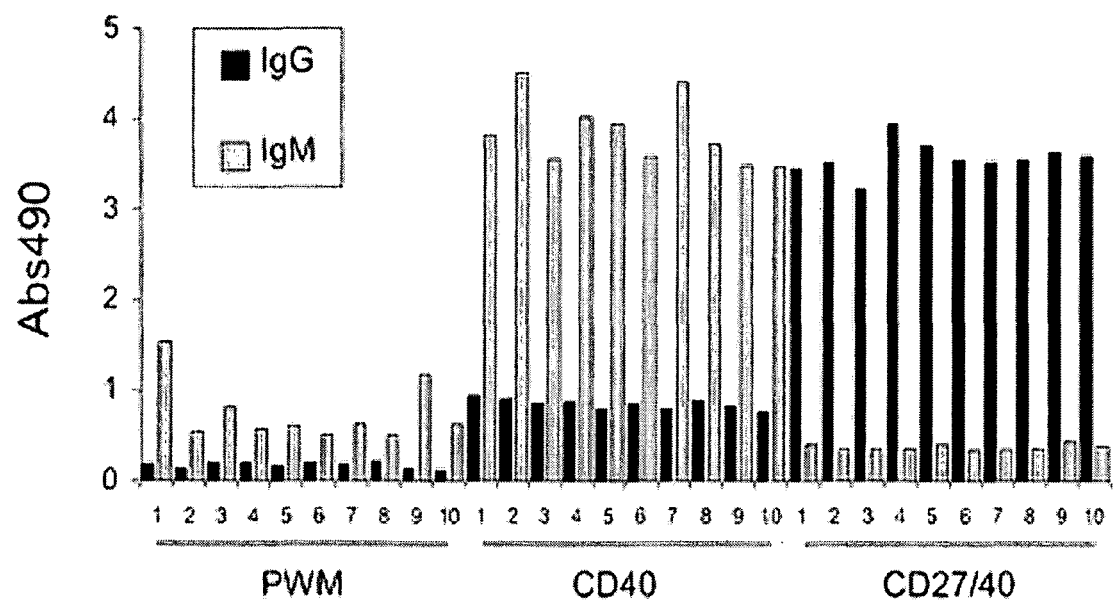
FIG. 1 is a graph showing the IgG and IgM profile of human immunoglobulins secreted by different hybridoma pools. The different hybridoma pools were generated from three different B-lympocyte populations. Human PBMCs used for cell fusion were prepared by 1) treatment with pokeweed mitogen (PWM), 2) culture on a tCD40L monolayer in the presence of IL-4, IL-10, and cyclosporine, or 3) pre-selection for expression of CD27 followed by culture on the tCD40L monolayer in the presence of IL-4, IL-10, and cyclosporine. Following fusion and HAT selection, each hybridoma pool supernatant was tested by ELISA for expression of IgM and IgG immunoglobulins. Absorbance values are shown for each hybridoma pool were tested at 490 nm and normalized to the positive serum controls for the ELISAs.

The present invention provides a novel cell-selection and in vitro culture strategy for using peripheral blood B-cells to generate libraries of stable hybridomas expressing affinity-matured, antigen-specific human IgG antibodies. As such, the invention provides an enriched population of B-cells that secrete IgG antibodies for generating a hybridoma library. The method includes culturing CD27+ B cells preferably in the presence of IL-4, IL-10, and CD40L, prior to fusion with a fusion partner for the generation of a hybridoma library.

The methods of the invention reduce the background of IgM secreting hybridomas because the method includes the use of CD27+ B cells. CD27 is a marker of post germinal center B-cells that have undergone somatic hypermutation and class switching. The treatment of CD27+ B cells with IL-4, IL-10, and CD40L further induces a class switch among IgM+IgD+CD27+ B cells. Therefore, CD27+ B cells treated with IL-4, IL-10, and CD40L provide for B cell population that is enriched for cells that secrete IgG antibodies. The fusion of CD27+ B cells treated with IL-4, IL-10, and CD40L with a fusion partner results in the generation of hybridomas that secrete IgG antibodies at an increased frequency.

Also provided are hybridoma libraries generated from the fusion of CD27+ B cells treated with IL-4, IL-10, and CD40L with a fusion partner. The libraries provide a larger percentage of cells that secrete IgG antibodies compared to known prior art human antibody hybridoma libraries. The libraries are also enriched for IgG antibodies relative to IgM antibodies, in part because culturing the CD27+ B cells in the presence of IL-4, IL-10, and CD40L induces a class switch in IgM+IgD+CD27+ B cells. The libraries are advantageous compared to the prior art because of the in vitro class switch step facilitates cloning of antibody variable domains from post-germinal center IgM antibodies in the more useful IgG isotype. The libraries of the present invention differ from libraries of the prior art that are made from B-cells selected for the expression of IgG antibodies prior to fusion, because they express IgG antibodies that originated in B-cells that had expressed IgM antibodies prior to cell culture and fusion and would therefore have been lost by a selection step that selects only for IgG-expressing B-cells.

The invention provides a method of creating a library of hybridomas that consist essentially of cells derived from post-germinal center B-cells. This is an important technical advance over the prior art methods because it streamlines cloning of antigen-specific hybridomas by reducing the background of hybridomas that express pre-germinal center cell antibodies, such as IgM antibodies. Prior art hybridoma libraries typically contain about 15% hybridomas that secrete post-germinal center cell antibodies because only about 15% of the post-germinal center B-cell population are present in total peripheral blood. The libraries created using CD27+ B cells cultured in the presence of at least IL-4, IL-10, and CD40L are enriched for IgG antibodies relative to IgM antibodies, because the culture conditions of the invention serve to induce class switch in IgM+IgD+CD27+ B cells and because the CD27 selection step prevents the incorporation of IgM+IgD+CD27− cells, which express low-affinity un-mutated (natural) IgM antibodies, into the libraries. This is an advancement in hybridoma technology by way of increasing the yield of IgG antigen-specific antibodies.

Post Germinal Center B Cells

CD27 is a marker for post-GC B cells. A cell that is "CD27+" or that "expresses CD27" is contrasted herein to a cell that is CD27− or does not express a detectable level of CD27. The present invention encompasses methods and kits for the isolation and expansion of CD27+ B cells. The term "enriched", as used herein refers to at least 20%, preferably at least 30%, more preferably at least 40%, even more preferably at least 50%, even more preferably at least 60%, even more preferably at least 70%, even more preferably at least 80%, even more preferably at least 90%, and even more preferably 100% more than a sample that is not enriched with respect to B cells of the CD27+ phenotype. CD27+ B cells can be isolated from peripheral blood of an immunized animal, preferably a human.

CD27+ B-cells can be isolated from peripheral blood from any known methods in the art. For example, an anti-CD27 antibody can be used to isolate CD27+ B cells from a peripheral blood sample. The method comprises contacting a cell population believed to include B cells expressing CD27 on their surface with an anti-CD27 antibody and substantially separating the CD27+ cell-antibody complex from a population of peripheral blood mononuclear cells.

The anti-CD27 antibody may be attached to a solid support to allow for separation. Procedures for separation may include magnetic separation, using antibody-coated magnetic beads or dynal beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate cell separation include fluorescence activated cell sorters, which can have varying degrees of sophistication, e.g., a plurality of color channels, low angle and obtuse light scattering detecting channels, impedance channels, etc., as well as magnetic activated cell sorters.

The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

Anti-CD27 antibodies can be conjugated to biotin, which then can be removed with avidin or streptavidin bound to a support, or fluorochromes, which can be used with a fluorescence activated cell sorter (FACS), to enable cell separation. For example, cells expressing CD27 are separated from other cells by the cell-surface expression of CD27. Conveniently, the anti-CD27 antibodies may be conjugated with markers, such as magnetic beads, which allow for direct separation, biotin, which can be removed with avidin or streptavidin bound to a support, fluorochromes, such as FITC, which can be used with a fluorescence activated cell sorter, or the like, to allow for ease of separation of the particular cell type. Any cell separation technique discussed herein may be employed which is not unduly detrimental to the viability of the remaining cells. Other cell separation techniques include, but are not limited to, dense particles for density centrifugation, an adsorption column, an adsorption membrane, and the like.

Where the anti-CD27 antibody is conjugated to a magnetic bead, a population of peripheral blood derived mononuclear cells is contacted with the magnetic bead-antibody conjugate under conditions suitable for binding of the antibody conjugate to the CD27 antigen displayed on the surface of post GC cells. After incubation under conditions suitable for binding, such as, but not limited to, an incubation at 4° C. for 20 minutes, the population of B-cells positive for the CD27 antigen are selected by passing the entire sample through a magnetic-based separation apparatus. Upon evacuation or elution of free solution from the apparatus, only the magnetically-retained marker-containing cells remain. The CD27+ B cells are then eluted from the apparatus, resulting in an enriched, isolated or purified population of CD27+ B cells.

An advantage of using CD27+ B cells over the standard unenriched population of human splenic mononuclear cell populations or even PBMC populations is that cultured CD27+ B cells have undergone somatic hypermutation and therefore express affinity-matured antibodies. Removing the CD27− B cell population from a fusion experiment used to generate a hybridoma library reduces the background of hybridoma cells that express un-mutated IgM antibodies that have low potential for value as diagnostic reagents or therapeutics. This improves the likelihood that a hybridoma expressing a useful antibody can be identified and expanded as a monoclonal cell.

Culturing

CD27+ B cells can be cultured according to standard culturing procedures. For example, following their isolation, CD27+ B cells are incubated in cell medium in a culture apparatus for a period of time or until the cells reach confluency before passing the cells to another culture apparatus. The culturing apparatus can be of any culture apparatus commonly used in culturing cells in vitro. Preferably, the level of confluence is greater than 70% before passing the cells to another culture apparatus. More preferably, the level of confluence is greater than 90%. A period of time for incubation can be any time suitable for the culture of cells in vitro. CD27+ B cell medium may be replaced during the culture of the CD27+ B cell at any time. Preferably, the CD27+ B cell medium is replaced every 3 to 4 days. CD27+ B cells are then harvested from the culture apparatus whereupon the CD27+ B cells can be used immediately or cryopreserved to be stored for use at a later time.

"Cell culture" refers generally to cells taken from a living organism and grown under controlled condition. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the "doubling time".

In preparation for fusion with a fusion partner for hybridoma generation, CD27+ B cells are cultured in the presence of IL-4, IL-10, and CD40L. The combination of IL-4, IL-10, and CD40L in the culture medium allows for the CD27+ B cells to undergo isotype switching or class switching. For example, IgD+IgM+CD27+ B cells can be induced to undergo isotype switching to IgG when cultured in the presence of IL-4, IL-10, and CD40L. When IgD+IgM+CD27+ B cells are incubated in the presence of IL-4, IL-10, and CD40L, the cells undergo a differentiation program that recapitulates the features characteristic of normal GC B cell maturation that occurs in vivo, such as somatic hypermutation and affinity selection resulting in the class switch to IgG.

The CD27+ B cells cultured in the presence of IL-4, IL-10, and CD40L can be fused with a fusion partner to generate human B cell hybridomas. The advantage of using the treated CD27+ B cells in the generation of hybridomas is that a higher percentage of cells in the hybridoma library secrete IgG antibodies.

The. CD40L used in the method of the invention can be isolated from cells which naturally express CD40L, or can be purified from cells which have been altered to express CD40L. Soluble CD40L can be added to the culture medium for culturing with CD27+ B cells. Alternatively, the CD27+ B cells can be cultured on a feeder layer, where the feeder cells secrete CD40L or express CD40L on their cell surface. Preferably, the CD27+ B cells are cultured with tCD40L cells. A CD40 stimulating activity can also be provided in the form of a peptide or antibody molecule that binds to CD40 and has a stimulatory capability similar to that of CD40L. The peptide or antibody molecule may be provide in solution or bound to a feeder cell layer, such as a cell that expresses a protein that binds to an antibody molecule, for example a cell that expresses Fc gamma RII/CDw32 receptor protein.

The cytokines useful in the method of the invention (e.g., IL-4 and IL-10) can be obtained by any known method in the art. The sources of IL-4 and IL-10 have been described and the DNA sequences encoding the molecules are also known. Therefore, natural or recombinant forms of IL-4 and IL-10 can be used for the culturing of CD27+ B cells. The amount of IL-4 supplemented to the medium can range from 0.1 ng/ml to 0.2 µg/ml (and any integer value in between). Preferably, 2 ng/ml IL-4 is supplemented to the medium. The amount of IL-10 supplemented to the medium can range from 0.5 ng/ml to 1.0 µg/ml (and any integer value in between). Preferably, 10 ng/ml IL-4 is supplemented to the medium.

The percentage of B cells that produce an antibody selective for a specific antigen can be increased by adding to the cell media an antigen which was used to immunize the host which was the source of the B cells. The combination of IL-4, IL-10, CD40L, and an antigen serves to further induce class switching of IgM+IgD+CD27+ B cells to IgG in vitro in an antigen specific manner. The antigen can be a compound that has been shown, or can be shown, to stimulate an antibody response when administered to a mammalian host. The antigen can be added to the culture medium prior to, concomitantly, or after adding IL-4, IL-10, and CD40L to the culture medium. Further, the skilled artisan can employ additional procedures to increase the antigenicity of an antigen as well as to insure that the antigen comes in contact with the cultured cells. Such procedures include coupling the antigen to a carrier to increase solubility or antigenicity.

After culturing the CD27+ B cells according to the methods of the invention, the CD27+ B cells can be fused with a fusion partner to generate a library of hybridomas.

Hybridoma Technology

CD27+ B cells prepared by the methods of the invention can be fused with any fusion partner to generate a hybridoma. A preferred fusion partner cell line is one that ectopically expresses hTERT and mIL-6. Preferably, a retroviral expression system is used to express mIL-6 and hTERT in the fusion partner cell line. A preferred fusion partner cell line is the B5-6T cell line which was deposited under the terms of the Budapest Treaty with the American Type Culture Collection, 10801 University Blvd, Manassas, Va. 20110-2209, USA, on Jan. 15, 2008 and assigned ATCC Accession No. PTA-8869. Other fusion partner cell lines may also be used, such as the SP2/mIL-6 MPT cell line, a murine cell line that also ectopically expresses mIL-6 and hTERT.

Generally, the CD27+ B cells are fused with a fusion partner and treated with 40-50% polyethylene glycol of MW 1000-4000, at about 37° C. for about 5-10 minutes to allow for the fusion. Alternatively, cell fusions can be induced by the standard method of electrofusion, in which an electrical charge is used to cause fusion of cell plasma mebranes. Following cell fusion, nascent hybrid cells are separated from the fusion mixture and propagated in media selective for the desired hybrids. When the hybrid cell is resistant to 8-azaguanine, the cell is conveniently selected by successive passaging of the cell on HAT or AH medium. Other selective procedures can be used depending on the nature of the cells used in fusion. Clones secreting antibodies having the required binding specificity are identified by assaying the antibody secreted into the culture medium for the ability to, bind to the botulinum neurotoxin polypeptide or an epitope thereof. The antibody producing cells having the desired specificity are subcloned by the limiting dilution technique and grown in vitro in culture medium, or are injected into selected host animals and grown in vivo.

The B5-6T fusion partner cell line stably expresses hTERT. It is further characterized in that it is capable of fusing with CD27+ B cells and generating hybridomas at a highly efficient rate. An advantage of using the B5-6T fusion partner cell line is that the B5-6T fusion partner cell line allows for the generation of hybridomas at an increased frequency. A characteristic of the B5-6T fusion partner cell line is the ability for the cell line to fuse with B-lymphocytes and produce hybridomas capable of surviving HAT selection at a highly efficient rate.

The B5-6T fusion partner cell line has the ability to produce hybridomas that are stable (i.e., hybridomas that maintain the ability to produce a particular antibody for an extended time periods, e.g., at least three rounds of culturing in vitro). A monoclonal-antibody producing hybridoma cell line produced using the B5-6T fusion partner cell line can be subcloned and subcultured for many passages, until sufficient numbers of cells are obtained to produce antibodies in gram quantities or greater.

Antibodies

In one embodiment, the invention is directed to a human anti-BoNT/A-binding antibody. The antibody comprises a heavy chain polypeptide comprising an antibody heavy chain variable domain comprising the amino acid sequence of SEQ ID NO: 4, and an antibody light chain polypeptide comprising and antibody light chain variable domain comprising the amino acid sequence SEQ ID NO: 8. The aforementioned amino acid sequences constitute the light and heavy chain polypeptides of the antibody secreted by hybridoma ATCC PTA-8870. The aforementioned amino acid sequences also constitute the light and heavy chain polypeptides of the 6A antibody.

In another embodiment, the invention is directed to a human anti-BoNT/A-binding antibody comprising a heavy chain polypeptide comprising the amino acid sequence of SEQ ID NO:. 2, and an antibody light chain polypeptide comprising the amino acid sequence SEQ ID NO: 6. The aforementioned amino acid sequences constitute the light and heavy chain polypeptides of the antibody secreted by hybridoma ATCC PTA-8870. The aforementioned amino acid sequences also constitute the light and heavy chain polypeptides of the 6A antibody.

In another embodiment, the antibody specifically binds to an epitope specifically bound by the 6A antibody. In another embodiment, the antibody comprises the 6A antibody. In a further embodiment, antigen-binding fragments that bind to an epitope specifically bound by the 6A antibody are provided.

The antibodies produced may be tested for the ability to bind BoNT/A or an epitope thereof. Antibodies may also be tested for the capacity to neutralize BoNT/A neurotoxin. Toxicity can be determined in vivo. For example, one can measure the toxicity of BoNT/A in a test animal (e.g. mouse) in the presence of one or more putative neutralizing antibodies. A neutralizing antibody can be combined with the botulinum neurotoxin prior to administration, or the animal can be administered with the antibody prior to, simultaneous with, or after administration of the neurotoxin.

A preferred in vitro assay for neutralizing activity uses a hemidiaphragm preparation (Deshpande et al., 1995, Toxicon 33:551-557). Briefly, purified antibodies are incubated with purified BoNT/A for 30 minutes at room temperature and then added to the tissue bath, resulting in a final antibody concentration of about $2.0 \times 10^{-8}$ M and a final neurotoxin concentration of about $2.0 \times 10^{-11}$ M. For each antibody studied, time to 50% twitch tension reduction is determined (e.g., three times for BoNT/A). Differences between times to a given (arbitrary) percentage (e.g. 50%) twitch reduction are determined by standard statistical analyses (e.g. two-tailed t test) at standard levels of significance (e.g., a P value of <0.05 considered significant).

Preferred antibodies of this invention act to neutralize (reduce or eliminate) the toxicity of botulinum neurotoxin (e.g. botulinum neurotoxin type A). In vivo neutralization measurements involve measuring changes in the lethality (e.g. $LD_{50}$ or other standard metric) due to a botulinum neurotoxin (e.g. botulinum neurotoxin type A) administration due to the presence of one or more antibodies being tested for neutralizing activity. The neurotoxin can be directly administered to the test organism (e.g. mouse) or the organism can harbor a botulism infection (e.g., be infected with Clostridium botulinum). The antibody can be administered before, during, or after the injection of BoNT/A neurotoxin or infection of the test animal. A decrease in the rate of progression, or mortality rate indicates that the antibody(s) have neutralizing activity.

The BoNT/A antibodies of the invention are useful in the treatment of pathologies associated with botulinum neurotoxin poisoning. The treatments essentially comprise administering to the poisoned animal (e.g. human or non-human mammal) a quantity of BoNT/A neutralizing antibody sufficient to neutralize (e.g. mitigate or eliminate) symptoms of botulinum neurotoxin poisoning.

Such treatments are most desired and efficacious in acute cases, such as where vital capacity is less than 30-40 percent of predicted and/or paralysis is progressing rapidly and/or hypoxemia with absolute or relative hypercarbia is present. Treatment with a neutralizing antibody can be provided as a adjunct to other therapies (e.g. antibiotic treatment).

Modification of Antibodies

The invention includes antibodies that specifically bind to an epitope specifically bound by the 6A antibody. The invention includes functional equivalents of the 6A antibody described herein. Functional equivalents have binding characteristics comparable to those of the 6A antibody, and include, for example, hybridized and single chain antibodies, as well as fragments thereof. Methods of producing such functional equivalents are disclosed in PCT Application WO 93/21319 and PCT Application WO 89/09622.

Functional equivalents of the 6A antibody further include antibodies or fragments thereof that have the same, or substantially the same, binding characteristics to those of the whole antibody. Such fragments may contain one or both Fab fragments or the $F(ab')_2$ fragment. Preferably the antibody fragments contain all six complement determining regions of the whole antibody, although fragments containing fewer than all of such regions, such as three, four or five complement determining regions, are also functional. The functional equivalents are members of the IgG immunolglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2a and IgG2b), gamma 3 (IgG3) and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

A) Phage Display

A phage display can be used to increase antibody affinity. To create antibodies of higher affinity for a botulinum toxin, for instance a BoNT/A-bind antibody, mutant single chain variable fragment (scFv) gene repertoires, based on the sequences disclosed herein can be created and expressed on the surface of phage. For a BoNT/A-binding antibody, mutant scFv gene repertoires based on the variable domains of antibody 6A are prepared. Display of antibody fragments on the surface of viruses which infect bacteria (bacteriophage or phage) makes it possible to produce human or other mammalian antibodies with a wide range of affinities and kinetic characteristics. To display antibody fragments on the surface of phage (phage display), an antibody fragment gene is inserted into the gene encoding a phage surface protein and the antibody fragment-fusion protein is expressed on the phage surface (McCafferty et al., 1990, Nature 348: 552-554; Hoogenboom et al., 1991, Nucleic Acids Res. 19:4133-4137).

Since the antibody fragments on the surface of the phage are functional, those phage bearing antigen binding antibody fragments can be separated from non-binding or lower affinity phage by antigen affinity chromatography (McCafferty et al., 1990, Nature 348:552-554). Mixtures of phage are allowed to bind to the affinity matrix, non-binding or lower affinity phage are removed by washing, and bound phage are eluted by treatment with acid or alkali. Depending on the affinity of the antibody fragment, enrichment factors of 20 fold-1,000,000 fold are obtained by single round of affinity selection.

One approach for creating mutant scFv gene repertoires involves replacing either the $V_H$ or $V_L$ gene from a binding scFv with a repertoire of $V_H$ or $V_L$ genes (otherwise known as chain shuffling) (Clackson et al., 1991, Nature 352:624-628). Such gene repertoires contain numerous variable genes derived from the same germline gene as the binding scFv, but with point mutations (Marks et al., 1992, Biotechnology 10:779-783). Using light or heavy chain shuffling and phage display, the binding avidities of BoNT/A-binding antibody fragment can be dramatically increased.

In order to generate an antibody having an increased affinity, during the screening for the antibody, the antigen concentration is decreased in each round of selection, reaching a concentration less than the desired $K_d$ by the final rounds of selection. This results in the selection of a desired antibody on the basis of affinity (Hawkins et al., 2002, J. Mol. Biol. 226: 889-896).

B) Site Directed Mutagenesis

To generate a BoNT/A-binding antibody, site directed mutagenesis is based on the variable domains of the antibody 6A. It is well known in the art that mutating amino acids that contact ligand has been shown to be an effective means of increasing the affinity of one protein molecule for its binding partner (Lowman et al., 1993, J Mol. Biol. 234:564-578; Wells, 1990, Biochemistry 29:8509-8516). The majority of antigen-contacting, amino acid side chains in an antibody are located in the complementarity determining regions (CDRs). Three of the CDRs occur in the $V_H$ (CDR1, CDR2, and CDR3) and three in the $V_L$ (CDR1, CDR2, and CDR3) (Chothia et al., 1987, J. Mol. Biol. 196:901-917; Chothia et al., 1986, Science 233:755-8; Nhan et al., 1991, J. Mol. Biol. 217:133-151). These residues contribute the majority of binding energetics responsible for antibody affinity for antigen.

The CDRs are separated by framework regions. The framework regions spatially orient the CDR regions to shape the antigen-binding structure. Mutations to residues in either CDR regions or framework regions may alter and/or improve the binding characteristics of an antibody. Due to their structural role, changes to residues in framework regions may result in improperly folded antibody structures that may be inactive (Shlomchik et al, 1989, Prog Immunol. 7:415-423). Consequently, changes to framework region residues should be conservative changes and should preserve hydrophobic packing interactions and buried salt bridges. The determination of which amino acids in an immunoglobulin protein sequence contribute to which domains is well understood in the art. See Lefranc et al., (2005, Nucleic Acids Res 33:D593-D597).

CDR and FR residues are determined according to a standard sequence definition (Kabat et al., Sequences of Proteins of Immunological Interest, National Institutes of Health, Bethesda Md. (1987), and a structural definition (as in Chothia and Lesk, J. Mol. Biol. 196:901-917 (1987). Where these two methods result in slightly different identifications of a CDR, the structural definition is preferred, but the residues identified by the sequence definition method are considered important FR residues for determination of which framework residues to import into a consensus sequence.

Accordingly, mutation of the CDRs and screening of the resulting mutants against BoNT/A or the epitopes thereof identified herein, may be used to generate BoNT/A-binding antibodies having improved binding affinity to an epitope and/or bind with higher affinity to specific sub-serotypes (Smith et al., 2005, Infect. Immun. 73:5450-5457).

In a preferred embodiment, each CDR is randomized in a separate library. To simplify affinity measurements, existing antibodies or other lower affinity BoNT/A-binding antibodies, are used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al., 1993, J. Mol. Biol., 234:564-578).

To increase the affinity of BoNT/A-binding antibodies, amino acid residues located in one or more CDRs (e.g. 9 amino acid residues located in $V_L$ CDR3) are partially randomized by synthesizing a "doped" oligonucleotide in which the wild type nucleotide occurred with a frequency of about for example 49%. The oligonucleotide is used to amplify the remainder of the BoNT/A-binding scFv gene(s) using PCR.

For example, in one embodiment, to create a library in which $V_H$ CDR3 is randomized, an oligonucleotide is synthesized which anneals to the BoNT/A-binding antibody $V_H$ framework 3 and encodes $V_H$ CDR3 and a portion of framework 4. At the four positions to be randomized, the sequence "NNS" can be used, where N is any of the 4 nucleotides, and S is "C" or "T". The oligonucleotide is used to amplify the BoNT/A-binding antibody $V_H$ gene using PCR, creating a mutant BoNT/A-binding antibody $V_H$ gene repertoire. PCR is used to splice the $V_H$ gene repertoire with the BoNT/A-binding antibody light chain gene, and the resulting scFv gene repertoire is cloned into a phage display vector. Ligated vector DNA is used to transform electrocompetent E. coli to produce a phage antibody library.

To select higher affinity mutant scFv, each round of selection of the phage antibody libraries is conducted on decreasing amounts of BoNT/A, as described elsewhere herein. Typically, 96 clones from the third and fourth round of selection are screened for binding to the BoNT/A antigen by ELISA on 96 well plates.

Other methods known in the art and used for mutagenizing antibodies include error-prone PCR, over-expression of dominant-negative mismatch repair proteins (WO 2004/046330), parsimonius mutagenesis (Razai et al., 2005, J Mol Biol. 351:158-169) and chemical mutagenesis. See also: Chowdhury et al (2005, Methods 36:11-27) and Carter (2006, Nat Rev Immunol. 6:343-357). Identification of antibodies with desirable properties can be achieved using a variety of common screenin methods (Hoogenboom, 2005, Nat Biotechnol. 23:1105-1116).

C) Creation of Botulinum Neurotoxin-Binding (scFv'), Homodimers

To create botulinum neurotoxin-binding (scFv')$_2$ antibodies, two botulinum neurotoxin-binding scFvs are joined, either through a linker (e.g., a carbon linker, a peptide, etc.) or through a disulfide bond between, for example, two cysteines. Thus, for example, to create disulfide linked botulinum neurotoxin-binding scFv, a cysteine residue can be introduced by site directed mutagenesis.

In a particularly preferred embodiment, the (scFv')$_2$ dimer is created by joining the scFv fragments through a linker, more preferably through a peptide linker. This can be accomplished by a wide variety of means well known to those of skill in the art. For example, one preferred approach is described by Holliger et al., 1993, Proc. Natl. Acad. Sci. USA 90:6444-6448 (see also WO 94/13804).

Typically, linkers are introduced by PCR cloning. For example, synthetic oligonucleotides encoding the linker can be used to PCR amplify the BoNT/A-binding antibody $V_H$ and $V_L$ genes which are then spliced together to create the BoNT/A-binding diabody gene. The gene is then cloned into an appropriate vector, expressed, and purified according to standard methods well known to those of skill in the art.

D) Preparation of Botulinum Neurotoxin-Binding (scFv)$_2$, Fab, and (Fab')$_2$ molecules BoNT/A-binding antibodies, such as a BoNT/A-binding scFv, or variant(s) with higher affinity, are suitable templates for creating size and valency variants. For example, a BoNT/A-binding (scFv')$_2$ is created from a parent scFv derived from the variable domains of antibody 6A, as described above. An scFv gene can be excised using appropriate restriction enzymes and cloned into another vector.

A botulinum neurotoxin-binding Fab is expressed in E. coli using an expression vector similar to the one described by Better et. al., 1988, Science 240:1041-1043. To create a BoNT/A-binding Fab, the $V_H$ and $V_L$ genes are amplified from the scFv using PCR. The $V_H$ gene is cloned into an expression vector (e.g., a PUC119 based bacterial expression vector) that provides an IgG $C_{H1}$ domain downstream from, and in frame with, the $V_H$ gene. The vector also contains a leader sequence to direct expressed $V_H$-$C_{H1}$ domain into the periplasm, a leader sequence to direct expressed light chain into the periplasm, and cloning sites for the light chain gene. Clones containing the correct VH gene are identified, e.g., by PCR fingerprinting. The $V_L$ gene is spliced to the $C_L$ gene using PCR and cloned into the vector containing the $V_H C_{H1}$ gene.

Genetic Modification

In addition to obtaining botulinum neurotoxin-binding antibodies from a hybridoma, the antibodies can also be generated by cloning antibody genes into one or more expression vectors, and transforming the vector into a cell line such as the cell lines typically used for expression of recombinant or humanized immunoglobulins.

The genes encoding the heavy and light chains of immunoglobulins secreted by the cell lines are cloned according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains are cloned from the antibody secreting cell's genomic DNA or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the heavy and light chains of the antibodies or portions thereof can be obtained and used in accordance with recombinant DNA techniques for the production of the specific immunoglobulin, immunoglobulin chain, or variants thereof, in a variety of host cells or in an in vitro translation system. For example, the nucleic acids, including cDNAs, or derivatives thereof encoding variants such as a the heavy and light chains, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

The heavy and light chains, or portions thereof, can be assembled in two different expression vectors that can be used to cotransfect a recipient cell. Each vector can contain two selectable genes, one for selection in a bacterial system and one for selection in a eukaryotic system. These vectors allow for the production and amplification of the genes in bacterial systems, and subsequent cotransfection of eukaryotic cells and selection of the cotransfected cells. The selection procedure can be used to select for the expression of immunoglobulin chain genes introduced on two different DNA vectors into a eukaryotic cell.

Alternatively, the genes encoding a heavy chain and light chain may be expressed from one vector. Although the light and heavy chains are coded for by separate genes, they can be joined, using recombinant methods. For example, the two polypeptides can be joined by a synthetic linker that enables them to be made as a single protein chain in which the VL and VH regions pair to form monovalent molecules (known as single chain Fv (scFv); see e. g. , Bird et al., 1988, Science 242: 423-426; and Huston et al. , 1988, Proc. Natl. Acad. Sci. USA 85 : 5879-5883).

The invention provides for an isolated nucleic acid molecule comprising a nucleic acid sequence encoding at least a heavy and a light chain variable region. A nucleic acid molecule comprising sequences encoding both the light and heavy chain variable regions can be engineered to contain a synthetic signal sequences for secretion of the immunoglobulin chains when produced in a cell. Furthermore, the nucleic acid molecule comprising both the heavy and light chain variable regions can contain specific DNA links which allow for the insertion of other immunoglobulin sequences and maintain the translational reading frame so to not alter the amino acids normally found in immunoglobulin chains. In particular, the nucleic acid molecule comprises sequences that encode the heavy chain variable domain comprising the amino acid sequence SEQ ID NO: 4 and the antibody light chain variable domain comprising the amino acid sequence SEQ ID NO: 8. In another aspect, the nucleic acid molecule comprises sequences of SEQ ID NO: 3 and SEQ ID NO: 7.

The invention also provides for an isolated nucleic acid molecule comprises sequences that encode the heavy chain polypeptide comprising the amino acid sequence SEQ ID NO: 2 and the antibody light chain polypeptide comprising the amino acid sequence SEQ ID NO: 6. In another aspect, the nucleic acid molecule comprises sequences of SEQ ID NO: 1 and SEQ ID NO: 5.

In accordance with the present invention, nucleotide sequences coding for heavy and light chains may be inserted into an appropriate expression vector. This vector which contains the necessary elements for transcription and translation of the inserted protein-coding sequence so as to generate recombinant DNA molecules that direct the expression of heavy and light chain immunoglobulins for the formation of an antibody.

In addition to the DNA segments encoding BoNT/A-binding immunoglobulins or fragments thereof, other substantially homologous modified immunoglobulins can be readily designed and manufactured utilizing various recombinant DNA techniques known to those skilled in the art such as site-directed mutagenesis. Such modified segments will usually retain antigen binding capacity and/or effector function. Moreover, the modified segments are usually not so far changed from the original genomic sequences of the antibody producing cell to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

A variety of methods can be used to express genes in a cell. Nucleic acids can be cloned into a number of types of vectors. However, the present invention should not be construed to be limited to any particular vector. Instead, the present invention should be construed to encompass a wide plethora of vectors which are readily available and/or well-known in the art. For example, an the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (1989), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. Preferably, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Another example of a viral vector is a Moloney Murine Leukemia Virus (MoMuLV) vector. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Retroviral vectors have been used extensively to deliver genes into a host cell or animal. Retroviral integration can take place at many locations. Retroviral insertion biases have been estimated by a variety of methods reviewed in Uren et al., 2005 Oncogene 24: 7656-7672. There is evidence that there is a preference for integration close to DNAseI sensitive and/or hypomethylated regions suggesting that retroviral integration has a tendency to insert within actively transcribed regions of the genome. Other evidence suggests that retroviral integration preferentially occurs near gene promoters. Generally, the evidence suggests that retroviral integration is correlated with the target DNA's local characteristics, including conformation and methylation status, gene density, chromatin conformation, host DNA associated proteins and local transcriptional activity. Accordingly, retroviral integration is partially affected by nucelosome structure rather than any particular sequence specificity. Thus, the integration site is unpredictable.

For expression of the desired gene, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (1989). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the desired gene(s), the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. and Ausubel et al.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Cells that have undergone alteration of. their DNA in order to cause such ectopic expression can be identified by single cell cloning and analyzing genomic DNA of the cloned cells for the presence of the altered DNA sequences using PCR with primers specific for the altered DNA sequences.

Cells that have integrated an ectopic gene into the genome of a cell can be identified by single cell cloning and analyzing genomic DNA of the cloned cells for the presence of the ectopic telomerase gene using PCR with primers specific for the altered DNA sequences. Expression of the ectopic gene can be confirmed with RT-PCR.

Therapeutic use and Pharmaceutical Compositions

One skilled in the art can readily determine an effective amount of botulinum neurotoxin-neutralizing antibody to be administered to a given subject, by taking into account factors such as the size and weight of the subject; the extent of disease penetration; the age, health and sex of the subject; the route of administration; and whether the administration is regional or systemic. Generally, the amount of antibody administered to a subject depends upon the amount of botulinum neurotoxin that needs to be neutralized and the amount of botulinum neurotoxin-neutralizing activity exhibited by the antibodies. Those skilled in the art may derive appropriate dosages and schedules of administration to suit the specific circumstances and needs of the subject. For example, suitable doses of each antibody to be administered can be estimated from the amount of botulinum neurotoxin to which a subject has been exposed, or the amount of botulinum neurotoxin to which the subject is in risk of being exposed. Typically, dosages of antibody are between about 0.001 mg/kg and about 100 mg/kg body weight. In some embodiments, dosages are between about 0.01 mg/kg and about 60 mg/kg body weight.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

A mixture of botulinum neurotoxin-neutralizing human antibodies can be administered in equimolar concentrations to a subject in need of such treatment. In another instance, the antibodies are administered in concentrations that are not equimolar. In other instances, the antibodies are administered as equal amounts of protein, by weight, per kilogram of body weight. For example, the antibodies can be administered in equal amounts, based on the weight of the subject. In another instance, the antibodies are administered in unequal amounts. In yet other instances, the amount of each antibody to be administered is based on its neutralizing activity. For example, a mixture with between about 1 IU/kg body weight and about 50 IU/kg body weight of botulinum neurotoxin-neutralizing activity can be administered.

In general, the schedule or timing of administration of a mixture of botulinum neurotoxin-neutralizing human antibodies is according to the accepted practice for the procedure being performed.

When used in vivo, the antibodies, either in their native form and/or in a recombinant form, are preferably administered as a pharmaceutical composition, comprising a mixture, and a pharmaceutically acceptable carrier. The antibodies may be present in a pharmaceutical composition in an amount from 0.001 to 99.9 wt %, more preferably from about 0.01 to 99.0 wt %, and even more preferably from 0.1 to 50 wt %. To achieve good plasma concentrations, an antibody, or a combination of antibodies, may be administered, for example, by intravenous injection, as a solution comprising 0.1 to 1.0% of the active agent.

The botulinum neurotoxin-neutralizing antibodies are useful for prophylactic and/or therapeutic treatment. The antibodies can be a component of a pharmaceutical composition. The pharmaceutical compositions of this invention are particularly useful for parenteral administration, such as intravenous administration or administration into a body cavity or lumen of an organ. The compositions for administration will commonly comprise a solution of botulinum neurotoxin-neutralizing antibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of botulinum neurotoxin-neutralizing in these formulations can vary widely, and will be selected primarily based on fluid volumes, viscosities, body weight and the like in accordance with the particular mode of administration selected and the subject's needs.

Thus, a typical pharmaceutical composition for intravenous administration would be about 0.1 to 10 mg per subject per day. Dosages from 0.1 up to about 100 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., Mack Publishing Company, Easton, Pa. (1980).

The compositions containing the antibody of the present invention can be administered for therapeutic treatments. In therapeutic applications, preferred pharmaceutical compositions are administered in a dosage sufficient to neutralize (mitigate or eliminate) BoNT/A (e.g., reduce or eliminate a symptom of BoNT/A (botulism)). An amount adequate to accomplish this is defined as a "therapeutically effective dose." Amounts effective for this use will depend upon the severity of the disease and the general state of the subject's health.

Single or multiple administrations of the compositions may be administered depending on the dosage and frequency as required and tolerated by the subject. In any event, the composition should provide a sufficient quantity of the proteins of this invention to effectively treat the subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLE 1

Isolation and Culturing of CD27+ B Cells

Heparinized peripheral blood was obtained following informed consent from volunteers vaccinated with the pentavalent botulinum toxoid vaccine in accord with a protocol approved by the Institutional Review Board of the Thomas Jefferson University. All BoNT-immune blood samples were obtained on the 8th day following the last dose of the pentavalent botulinum toxoid vaccine. The peripheral blood mononuclear cell (PBMC) fraction was isolated using gradient density centrifugation with FicollPaque PLUS (GE Healthcare, Piscataway, N.J.). Purified PBMCs were used fresh or after frozen storage in 90% heat-inactivated fetal calf serum (FCS, Invitrogen, Carlsbad, Callif.), 10% DMSO (Sigma-Aldrich, St. Louis, Mo.). CD27+ B cells were isolated from the PBMC sample using anti-CD27 magnetic beads according to the manufacture's protocol (Miltenyl Biotec, Auburn, Calif.).

The CD27+ B cells were cultured in the presence of IL-4, IL-10, and CD40L as follows. CD40L was provided to the culture medium by way of the tCD40L cells. tCD40L cells are mouse fibroblasts transfected with CD40L that stably express CD40L (Schultze et al., 1997). To prepare the tCD40L monolayer, tCD40L cells were irradiated with 96 Gy plated at a density of $5 \times 10^4$/well in 12-well tissue culture plates (Corning, Corning, N.Y.). Culturing of tCD40L cells was in 45% F12, 45% DMEM, 10% IFS, L-glutamine and penicillin/streptomycin. CD27+ B cells cultured with the tCD40L cells were supplemented with 10% human serum, IL-4 (2 ng/ml), IL-10 (10 ng/ml), transferrin (50 micrograms/ml), cyclosporine A ($5.5 \times 10^{-4}$ M), L-glutamine (2 mM), and optionally an antigen such as BoNT/A or recombinant 50 kD C-terminal BoNT/A domain (Kiyatkin et al., 1997 Infect Immun 65: 4586-4591), hereinafter "HC50A" (5 micrograms/ml), and penicillin/streptomycin (Sigma-Aldrich).

EXAMPLE 2

Generation of Hybridomas Producing Human IgGs

The following experiments were designed to generate hybridomas that secrete human antibodies resulting from the fusion between a fusion partner cell line and cultured CD27+ B cells. The experiments was designed to improve on the low yield of hybridomas that secrete IgG antibodies produced using PBMCs cultured either in the presence of pokeweed mitogen (PWM) or in the presence of IL-4, IL-10, and CD40L (see below; A. Initial Experiments: Fusion using non-CD27+ enriched B cells). The results presented herein demonstrate a method of increasing the yield of generating hybridomas that secrete IgG human antibodies using CD27+ B cells cultured in the presence of IL-4, IL-10, and CD40L.

A. Initial Experiments: Fusion Using Non-CD27+ Enriched B Cells

The fusion partner cell lines used in these experiments were the B5-6T Accession Number PTA-8869 and the MPT (SP2/mIL-6 MP hTERT) fusion partner cell (Dessain et al., 2004 J Immunol Methods 291: 109). Both fusion partner cell lines ectopically express mIL-6 and hTERT genes. Generally, production of a monoclonal antibody includes the fusion of an immortal cell with a primary B-lymphocyte to generate a hybridoma that secretes a monoclonal antibody.

This initial experiment was designed to use PBMCs for the generation of hybridomas in order to establish a baseline level of hybridomas produced using unselected CD27+ B cells. PBMCs were obtained by peripheral blood draw from volunteer subjects who had received 3-6 doses of the pentavalent botulinum toxoid vaccine. Samples were obtained on the 8th day following the last vaccine dose. PBMCs cultured either in the presence of pokeweed mitogen (PWM) or in the presence of IL-4, IL-10, and CD40L prior to fusion with the MPT fusion partner cell line. Hybrids were selected for expression of IgG antibodies reactive with BoNT/A and BoNT/B by ELISA. From 7 cell fusions performed with the MPT cell line, comprising 160 total wells screened, it was only observed that 1 well contained IgG antibodies specific for BoNT/A and 0 wells contained IgG BoNT/B antibodies. As summarized in Table 1, regardless of whether PMBCs were stimulated with PWM or cultured in the presence of IL-4, IL-10, CD40L ("CD40L/IL-4L/IL-10" in. Table 1), the fusion between PBMCs and the MPT fusion partner cells did not result in a high frequency of the desirable hybridomas, although the frequency was improved somewhat using B5-6T as the fusion partner. The results demonstrate a low yield of producing hybridomas that secrete IgG antibodies using B cells unselected for CD27 expression.

B. Fusion Using CD27+ Cells

In this experiment, fusions were carried out by first specifically isolating, expanding, and class-switching the CD27+ B cell subset cell population from PBMCs obtained from volunteer subjects who had received 3-6 doses of the pentavalent botulinum toxoid vaccine. Accordingly, CD27+ B cells were magnetically selected from the population of PBMCs. The CD27 marker correlates with the post-GC phenotype and expression of somatically mutated antibody genes (Klein et al., 1998; Tangye et al., 1998). This separation step can remove about 60% of peripheral blood B-cells that express un-mutated IgM antibodies. The isolated CD27+ B cell population was then cultured according to Example 1 on a tCD40L monolayer in the presence of IL-4 (2 ng/ml) and IL-10 (10 ng/ml) (designated as "27/40L/IL-4/IL-10" in Table 1). After 8 days in culture, the treated CD27+ B cells were fused with the B5-6T fusion partner cell line. From 2 fusions between the B5-6T cell line and treated CD27+ B cells, a total of 12 hybrid pools expressing IgG antibodies specific for BoNT/A and 14 specific for BoNT/B was obtained. These results demonstrate that using CD27+ B cells as the starting cell population and culturing them in the presence of IL-4, IL-10, and CD40L increases the frequency of generating desirable hybridomas.

C. Comparative Analysis of B-Cell Isolation and Culture Methods for Hybridoma Production This set of experiments was designed to directly compare the three different B cell preparation methods (PWM method, CD40L/IL-4/IL-10 method, and 27/40L/IL-4/IL-10 method) and their effects on the production of hybridoma following fusion with the B5-6T fusion partner.

A single PBMC sample was obtained from donor #4 following a sixth dose of vaccine (designated as Bot4_6 in Table 1). This sample was separated into three groups and were cultured under the following conditions:

1) PBMCs treated with PWM (the PWM method);
2) PBMCs treated with IL-4, IL-10, CD40L (the CD40L/IL-4/IL-10 method); and
3) CD27+ B cells treated with IL-4, IL-10, CD40L (the 27/40L/IL-4/IL-10 method).

It was observed that fusion with CD27+ B cells cultured in the presence of IL-4, IL-10, and CD40L resulted in a total of 8 hybridoma wells that were positive for IgG to BoNT/A and 16 were positive for BoNT/B. In contrast, PBMCs that were treated with PWM produced 2 wells positive for IgG specific for BoNT/A, and no wells positive for BoNT/B, while PBMCs treated with IL-4, IL-10, CD40L produced a total of 2 and 1 wells positive for BoNT/A and BoNT/B, respectively. The results demonstrate that treated CD27+ B cells gives rise to IgG secreting hybridomas at an increased frequency compared to methods that do not include treating an enriched population of CD27+ B cells with IL-4, IL-10, and CD40L. The results are summarized in Table 1.

These results demonstrate that the PBMCs processed according to the 27/40L/IL-4/IL-10 method resulted in an increased number of hybridomas produced following fusion with a fusion partner. The BoNT antibody data shown in Table 1 were combined to estimate differences in response rates for the three culture methods. For the counts of HC50A IgG responses, the model yielded significant differences among treatments: 27/40L/IL-4/IL-10 was significantly different from either CD40L/IL-4/IL-10 ($p<0.001$) or PWM ($p=0.002$), while CD40L/IL-4/IL-10 and PWM were not different ($p=0.796$). The response rate was estimated to be 5.5 times (95% CI: 4.5, 6.8) higher for 27/40L/IL-4/IL-10 than for CD40L/IL-4/IL-10 and 5.8 times (95% CI: 3.4, 10.0) higher for 27/40L/IL-4/IL-10 than for PWM. For counts of HC50B IgG responses, the model yielded significant differences among treatments. PWM was significantly different from CD40L/IL-4/IL-10 and 27/40L/IL-4/IL-10 ($p<0.001$), and 27/40L/IL-4/IL-10 was also significantly different from CD40L/IL-4/IL-10 ($p<0.001$). The response rate was estimated to be 15 times higher (95% CI: 12.9, 17.5) for 27/40L/IL-4/IL-10 than for CD40L/IL-4/IL-10. For PWM, no responses were observed, and the incidence rate ratio could not be estimated. These results demonstrate that the CD27 selection CD40L/IL-4/IL-10 culture method creates hybridoma libraries significantly enriched for antigen-specific IgG antibodies compared to other tested culture methods.

EXAMPLE 3

Application of the 27/40L/IL-4/IL-10 Method to Vaccinia Virus Antigens

The observation that CD27+ B cells cultured in the presence of IL-4, IL-10, CD40L resulted in more hybridomas was extended to determine whether hybridomas can be generated to produce antibodies specific for vaccinia virus antigens. PBMCs were drawn from a donor infected with vaccine virus. The time of blood drawn was approximately 3 weeks following the estimated date of exposure to the virus and while the subject was still symptomatic from the infection. The isolated PBMCs were prepared according to the PWM treatment or the CD27 selection/tCD40L monolayer culture in the presence of IL-4 and IL-10 and fused with the B5-6T fusion partner as discussed elsewhere herein. Following hybrid cell selection, hybridoma supernatants were assayed by ELISA for human IgG antibodies specific for whole vaccinia virus virions. From the unselected PBMC population cultured in the presence of PWM, only 1 of 20 wells was positive for vaccinia-specific human IgG, in contrast to 17 of 20 wells positive from the CD27 selected cell population cultured in the presence of IL-4, IL-10, and CD40L (Table 1).

TABLE 1

PBMC treatment affects yields of hybridomas secreting antigen-specific human IgG

| Sample | Treatment | Fusion Partner | Wells plated | HC50A n (%) | HC50B n (%) |
|---|---|---|---|---|---|
| Bot1_3 | PWM | MPT | 30 | 0(0) | NT |
| Bot6_3 | PWM | MPT | 30 | 0(0) | 0(0) |
| Bot6_4 | PWM | MPT | 20 | 0(0) | 0(0) |
| Bot4_6 | PWM | B5-6T | 20 | 2(10) | 0(0) |
| Bot4_6 | PWM | B5-6T | 20 | 0(0) | 0(0) |
| Bot1_4 | CD40L/IL-4/IL-10 | MPT | 20 | 0(0) | 0(0) |
| Bot1_3 | CD40L | MPT | 20 | 0(0) | 0(0) |
| Bot2_4 | CD40L | MPT | 20 | 0(0) | 0(0) |
| Bot5_4 | CD40L | MPT | 20 | 1(5) | 0(0) |
| Bot4_6 | CD40L | B5-6T | 20 | 1(5) | 0(0) |

TABLE 1-continued

PBMC treatment affects yields of hybridomas secreting antigen-specific human IgG

| Sample | Treatment | Fusion Partner | Wells plated | | HC50B n (%) |
|---|---|---|---|---|---|
| Bot4_6 | CD40L | B5-6T | 20 | 1(5) | 1(5) |
| Bot4_5 | 27/40L/IL-4/IL-10 | B5-6T | 20 | 8(40) | 8(40) |
| Bot1_6 | 27/40L/IL-4/IL-10 | B5-6T | 20 | 4(20) | 6(30) |
| Bot4_6 | 27/40L/IL-4/IL-10 | B5-6T | 20 | 2(10) | 2(10) |
| Bot4_6 | 27/40L/IL-4/IL-10 | B5-6T | 20 | 6(30) | 14(70) |
| | | | | *Vaccinia* n (%) | |
| Vacc | PWM | B5-6T | 20 | 1(5) | |
| Vacc | 27/40L/IL-4/IL-10 | B5-6T | 20 | 17(85) | |

Botulinum toxoid vaccine-exposed donors (Bot1, 2, 4, 5, 6) were sampled after doses 3, 4, 5 or 6 of the vaccine. PBMC's were culture prior to cell fusion with either pokeweed mitogen alone (PWM), stimulation with CD40L, IL-4 and IL-10 (CD40L/IL-4/IL-10), or first selected for CD27 expression and then cultured with CD40L, IL-4 and IL-10 (27/40L/IL-4/IL-10). Two different cell lines were used for these experiments, MPT2 and B5-6T. Experiments with Bot4_6 PBMCs were performed in parallel to enable a direct comparison of the cell preparation methods.

EXAMPLE 4

Comparison Between IL-10 and IL-21 in Culturing CD27+ B Cells for Fusion

This set of experiments was designed to demonstrate the differences between IL-10 and IL-21 when combined with IL-4 and CD40L in the preparation of CD27+ B cells for fusion with a fusion partner to produce a hybridoma library. It was observed that IL-10/IL-4/CD40L-treated CD27+ B cells gave rise to more antigen-specific hybridomas than IL-21/IL-4/CD40L-treated CD27+ B cells following fusion with a fusion partner.

PBMCs were obtained by peripheral blood draw from volunteer subjects who had received 3-6 doses of the pentavalent botulinum toxoid vaccine. Samples were obtained on the 8th day following the last vaccine dose. Peripheral blood mononuclear cells were magnetically selected for expression of CD27 and cultured on a tCD40L cell feeder layer in the presence of cyclosporine, IL-4 and either IL-10 or IL-21. The cells were then fused to the B5-6T cell line and cultured in HAT-selective medium for 2 weeks. The hybridoma supernatants were assessed for the presence of human antibodies that bind recombinant 50 kD C-terminal BoNT/A domain (HC50A) or recombinant 50 kD C-terminal BoNT/E domain (HC50E) by ELISA. It was observed that the treatment of CD27+ B cells with IL-10, IL-4, and CD40L produced more hybridomas secreting antibodies specific for botulinum neurotoxin HC50 C-terminal domains than did treatment of CD27+ B cells with IL-21, IL-4, and CD40L (Table 2). The results demonstrate that IL-21 cannot substitute for IL-10 in culturing CD27+ B cells in the presence of IL-4 and CD40L to produce a cell population that is desirable for cell fusion to produce a hybridoma library.

TABLE 2

| Treatment | HC50A IgG | HC50E IgG | Total |
|---|---|---|---|
| IL − 10 + IL − 4 + CD40L | 2 | 3 | 5 |
| IL − 21 + IL − 4 + CD40L | None | None | 0 |

EXAMPLE 5

Characterization of Antibodies

Hybridomas generated from CD27+ B cells cultured in the presence of CD40L, IL-4 and IL-10 were observed to primarily secreted IgG immunoglobulins. In contrast, hybridomas produced from unselected B-lymphocyte populations produced significant amounts of both IgM and IgG (FIG. 1). Based on these observations, the next set of experiments was designed to characterize the mutation status of immunoglobulin genes expressed by the hybridoma clones created from CD27+ B cells treated with IL-4, IL-10, and CD40L.

CD27-selected peripheral blood mononuclear cells were obtained from a subject exposed to either the pentavalent botulinum toxoid vaccine or to the vaccinia virus. The CD27+ B cells were treated with IL-4, IL-10, and CD40L and fused with a fusion partner cell line to generate either a BoNT-immune hybridoma library or a Vaccinia-immune hybridoma library. Consensus primers specific for VH3 and VH4 gene families were used to clone the heavy chain variable regions from the hybridoma libraries. A total of 26 functional heavy chain variable domain sequences were obtained from both the BoNT-immune library (designated as B1-B15) and the Vaccinia-immune library (designated as V1-V11) (FIG. 3). Gene sequences of the third complementarity determining regions (CDR3s) of all 26 heavy chain variable domain sequences were compared with germline sequences in the IMGT database using the V-Quest program (Lefranc et al., 2005). Two of the sequences contained no mutations in their CDR3 region (B3, V2), four sequences contained 1-2 mutations in their CDR3 region (B7, B10, V3, V5), and the other 21 sequences have an overall mutation rate from 1.1-12.0% in their CDR3 region. These results were highly similar in distribution to the mutation rates observed in CD27+ peripheral blood B-cells (Klein et al., 1998; Tian et al., 2007), and they indicate that the present invention creates hybridoma libraries that consist exclusively of antibodies derived from by post-germinal center B cells. The results of the mutation analysis is summarized in FIG. 3.

It was also observed that the monoclonal antibodies generated using the CD27+ B cells treated with IL-4; IL-10, CD40L exhibited characteristics typical of antibodies produced by post GC cells found in human peripheral blood B-cells. For example, the CDR3 lengths in the sequenced genes of immunoglobulin from the BoNT-immune library and Vaccinia-immune library ranged from 9-26 amino acids, with 12 of 26 CDR3 regions containing 20 or more amino acids (Brezinschek et al., 1995). Taken together, these data indicate that hybridoma libraries created from treated CD27+ B cells principally express IgG antibodies that reflect the affinity-matured antibody repertoire of the post-GC B-cell population. The generation of IgG secreting hybridoma libraries is an advantage over IgM secreting hybridoma libraries because IgG antibodies represent antibodies that have undergone somatic hypermutation and therefore have a higher affinity to their antigenic binding site.

The results demonstrate CD27-selection followed by in vitro expansion in the presence of IL-4, IL-10, and CD40L reduces the background of IgM-secreting hybridomas, enriches the resultant hybridoma libraries for secretion of post-GC IgG antibodies, and increases the yield of antigen-specific antibodies cloned. Because only about 15% of the post-GC B-cell repertoire in peripheral blood is class-switched, the expansion of CD27+ B cells in IL-4, IL-10, and CD40L allows for class-switching of approximately 40% of CD27+ B cell population that are IgM+IgD+ and therefore increases the percentage of IgG-expressing hybridoma population in the hybridoma library.

EXAMPLE 6

Generation of the 6A hybridoma and 6A Antibody

The 6A hybridoma was generated as follows. CD27+ B cells were isolated from peripheral blood lymphocytes from a volunteer donor vaccinated with pentavalent botulinum toxoid vaccine. The isolated CD27+ B cells were cultured on a CD40 ligand-expressing cell monolayer (tCD40L). The culture medium was supplemented with IL-4 and IL-10. The CD27+ B cells were then fused to the B5-6T fusion partner cell line and selected with HAT using standard techniques. Briefly, the cultured CD27+ B cells were fused to fusion partner cells at a 1:1 ratio using the stirring method with 50% polyethylene glycol (Sigma-Aldrich) and selection in HAT medium (Sigma-Aldrich). Fused cells were seeded in 48-well plates at a density of $2 \times 10^5$ B-cells per well in the presence of a feeder layer of $1 \times 10^5$ C57BL/6 thymocytes/well. Hybrid cells were cloned at 1 cell/well in 96-well plates with $1 \times 10^5$ C57BL/6 thymocytes/well. After 3-4 rounds of cloning, stable IgG-secreting hybridomas were adapted to IS MAB-CD (Irvine Scientific, Santa Ana, Calif.), plated at a density of $5 \times 10^5$ cells/ml in 100 ml culture and incubated for 5 days in a 500 ml roller bottle. Filtered supernatants were purified over Protein G Sepharose columns (GE Healthcare). Purity was assessed using SDS-PAGE (Invitrogen). Protein concentrations were determined using the NanoDrop spectrophotometer (NanoDrop Technologies, Wilmington, Del.).

Hybrid cell pools were tested for human antibodies secreted into their supernatants that specifically bound BoNT/A by ELISA. Cells in each positive pool were cloned by limiting dilution. The specificity of the secreted antibody for BoNT/A was verified by a limiting dilution ELISA.

To assay human BoNT immunoglobulins, 96-well Easy-Wash plates were coated at 4° C. overnight with 100 μl/well BoNT/A, BoNT/B, HC50A or HC50B, at 5 g/ml in PBS (Kiyatkin et al., 1997). Plates were washed with PBS/0.05% Tween-20 (Sigma-Aldrich) and then blocked for 1 hour at 37° C. with PBS/0.05% Tween-20/5% bovine calf serum/3% goat serum (Sigma-Aldrich). Hybridoma supernatants were added at 100 l/well and incubated for 2 hours at 37° C., followed by secondary antibodies, either murine antihuman IgG HRP (9040-05) or goat anti-human IgM HRP (2020-05) (Southern Biotechnology, Birmingham, Ala.). OPD was used as the colorimetric substrate; optical density (O.D.) at 490 nm was measured. Qualitative analysis of human immunoglobulins in hybridoma supernatants was performed as described (Dessain et al., 2004), using a polyclonal rabbit anti-human whole IgG (6145-01) (Southern Biotech) as a capture antibody and the HRP-conjugated anti-IgG and anti-IgM secondary antibodies. Light chains were assessed by capture of the antibodies with the polyclonal rabbit anti-IgG and detection of or light chains with HRP-conjugated specific goat polyclonal antibodies A5175 (lambda) and A7164 (kappa) (Sigma-Aldrich).

The hybridoma designated as 6A was chosen for further binding analysis based on positive results in the ELISA screening. The 6A antibody secreted from the 6A hybridoma was subjected to the Kinetic Exclusion Assay (KinExA) using a flow fluorimeter (Sapidyne Instruments, Boise, Id.) to determine solution phase affinity and association rate constants. KinExA experiments were performed at room temperature. Running buffer was Tris buffer saline (10TBS-10 mM tris, 100 mM NaCl, 0.02% NaN3, pH 8), while sample buffer was 10TBS augmented with 1 mM PMSF, 1 mg/ml BSA. HC50A was purified as described (Maksymowych and Simpson, 2004) and processed through a refinement step by passage over a Superdex S200 size exclusion column (GE Healthcare). Antigen concentrations were determined using the Edelhoch method and absorptivity coefficient of 87050 (Edelhoch, 1967). Equilibrium experiments were prepared by serially diluting HC50A into solutions with a constant concentration of antibody. Equilibration times were determined empirically by running solutions at multiple times until a stable calculated Kn was reached. Equilibrium experiments were performed at least 5 times.

Figure 2:
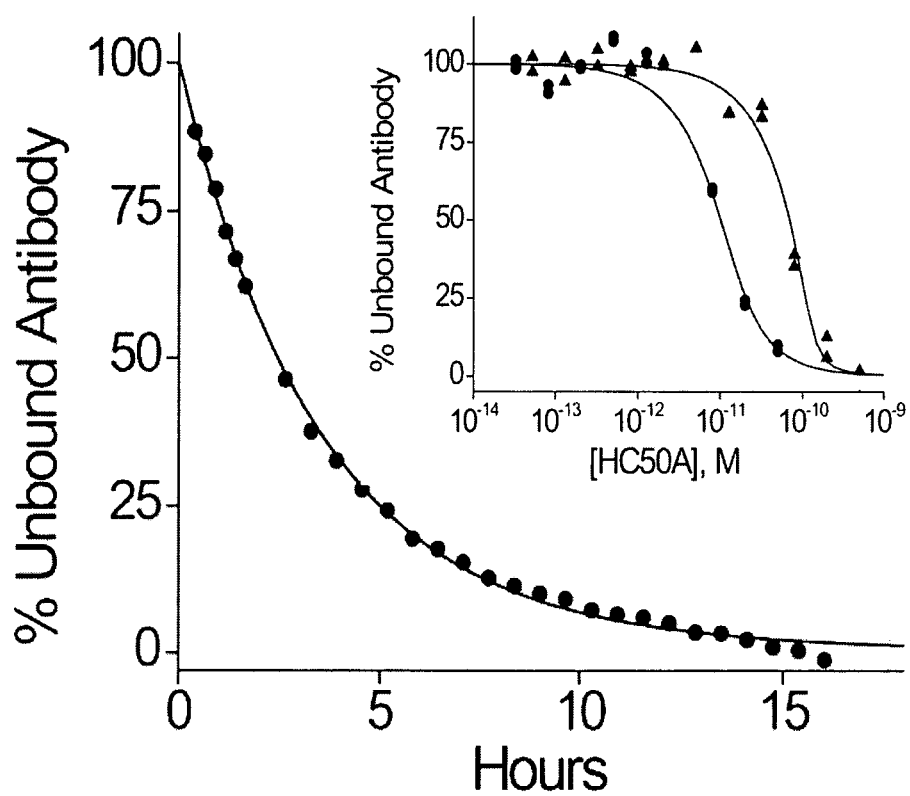
FIG. 2 is a graph showing the binding of antibody 6A to the C-terminal 50 kD domains of BoNT/A.

Association rate experiments were performed using the "Direct Kinetics" method, where binding of the 6A antibody and HC50A in a single reaction was followed as a function of time as the reaction progressed to equilibrium (Luginbuhl et al., 2006). All KinExA experiments used HC50A covalently attached to a polymethyl methacrylate (PMMA) beads (Sapidyne Instruments). In general, free antibody in the reaction mixtures was captured by passage over HC50-conjugated beads and detected with goat anti-human Rhodamine labeled secondary antibody (0.5 g/ml) (Jackson ImmunoResearch, West Grove, Pa.) (Luginbuhl et al., 2006). Equilibrium data were fit to a 1:1 binding model using manufacturer's software that included a drift correction factor (Version 2.4; Sapidyne Instruments). Kinetic experiments were fit to a general bimolecular association model included in the software. Dissociation rate constants were calculated as the product of $K_D \times k_{on}$. The 6A antibody was measured to have a $K_D$ value of $6.9 \times 10^{-12}$M for BoNT/A with an association rate ($k_{on}$) of $4.4 \times 10^5$ $M^{-1}$ $s^{-1}$ (FIG. 2).

The 6A hybridoma was deposited under the terms of the Budapest Treaty with the American Type Culture Collection, 10801 University Blvd, Manassas, Va. 20110-2209, USA, on Jan. 15, 2008 and assigned ATCC Accession No. PTA-8870.

EXAMPLE 7

Neutralization Activity of 6A Antibody 10 pg BoNT/A (~2.5 LD50) (Metabiologics) was incubated with 100 µg antibody or control cell culture medium for 1 hour at room temperature prior to intravenous administration into 25 gram Swiss-Webster mice, in accord with protocols approved by the Institutional Animal Care and Use Committee of Thomas Jefferson University. Mice were observed initially for 5 days following the injections (Pearce et al., 1994) and sacrificed if they appeared moribund. Mice receiving the 6A antibody survived, whereas mice receiving any of the other antibodies (1A, 15A, 31A) did not. However, it was observed that the 15A antibody delayed the onset of mortality (FIG. 4).

The 6A antibody was then tested to determine whether it could neutralize BoNT/A in both pre- and post-exposure intoxication models (FIG. 4). Groups of 3 mice received 500 µg 6A antibody intravenously, either 60 minutes before or 15 minutes after intravenous administration of BoNT/A. All mice in both groups survived, indicating the ability of the 6A antibody to effectively bind and neutralize BoNT/A within the murine blood circulation. Following the standard 5-day observation period, the mice were monitored for a total of 4 weeks and no late morbidity or mortality was observed.

The 6A antibody is unique in that it is the first fully human IgG that is capable of completely neutralizing a lethal dose of BoNT in vivo, although murine antibodies with this ability have been reported (Pless et al., 2001). Furthermore, 6A is able to protect mice in pre- and post-exposure prophylaxis models, which has not been demonstrated for any single BoNT neutralizing antibody. The high affinity and bound-state stability of the 6A antibody makes it an ideal component of oligoclonal antibody therapeutics for BoNT/A.

EXAMPLE 8

Cloning of Antibodies cDNAs of the heavy chain and light chain variable domains of the 6A, antibody was cloned from the hybridomas described elsewhere herein with standard RT-PCR techniques. Variable DNA sequences of BoNT-specific antibodies were amplified with consensus primer sets specific for human immunoglobulin heavy chains and kappa light chains (Campbell et al., 1992) and for lambda light chains (Coronella et al., 2000). RNA was isolated from hybridomas using RNA Stat 60 (Tel-Test, Inc., Friendswood, Tex.). Reverse transcriptase reactions were performed with Omniscript RT (Qiagen, Valencia, Calif.). PCR reactions were performed with Taq (Qiagen), for 30 cycles of 94° C., 15 sec; 55° C., 30 sec; 72° C., 60 sec. Amplified sequences were isolated by agarose gel electrophoresis followed by purification with the QiaQuick Gel Extraction kit, (Qiagen) and then sequenced by the Kimmel Cancer Center Nucleic Acid Facility. Non-specific immunoglobulin heavy chain sequences were amplified with RT-PCR with oligonucleotides specific for VH3 (V 10B with JH3) or VH4 (VH4B and VH6B with JH145) (Goossens et al., 1998; Coronella et al., 2002). The RT reaction was performed with Superscript II and oligo-dT primers (Invitrogen). PCR reactions were performed with the Expand High Fidelity PCR system (Roche) (25 cycles of 94° C., 15 sec; 55° C., 30 sec; 72° C., 60 sec-plus 5 sec increase every cycle for cycles 16-25) and cloned for sequencing using the Topo-TA cloning kit (Invitrogen). DNA sequences were analyzed using the V-Quest program (Lefranc et al., 2005).

The following are the sequences:

6A Heavy chain DNA sequence,
SEQ ID NO: 1
ATGGAGTTTGGGCTGAGCTGGGTTTTCCTTGTTACTATTTTAAAAGGTGT

CCAGTGTGAAGTGCAATTGGTGGAGTCTGGGGGAGGCGTGGTGAAGCCGG

GGGGGTCCCTGAGACTCTCCTGTACAGCTTTTGGATTCACGTTTGAGGAT

TTTGGCATGCACTGGGTCCGTCAAGCTCCAGGGAAGGGTCTGGAGTGGGT

CTCTCTTGTTAGTGGGAAGGTGGTAGCAAATACTATGCCGACTCTGTGA

AGGGCCGGTTCACCATCTCCAGAGACAACAAGAAGCACTCCCTGTATCTG

CACATGAACAGTCTGAAAACTGAGGACACCGCCTTGTATTACTGTGCAAA

AGATGTATGGACCTACCACTATGATAGCAGTGGTTACCAATACTACTACG

GTATGGACGTCTGGGGCCAAGGGACCACGGTCACCGTCTCCTCAGCAAGC

ACCAAAGC

6A Heavy chain AA sequence,
SEQ ID NO: 2
MEFGLSWVFLVTILKGVQCEVQLVESGGGVVKPGGSLRLSCTAFGFTFED

FGMHWVRQAPGKGLEWVSLVSGEGGSKYYADSVKGRFTISRDNKKHSLYL

HMNSLKTEDTALYYCAKDVWTYHYDSSGYQYYYGMDVWGQGTTVTVSSAS

TK

6A Heavy chain variable domain DNA sequence,
SEQ ID NO: 3
GAAGTGCAATTGGTGGAGTCTGGGGGAGGCGTGGTGAAGCCGGGGGGGTC

CCTGAGACTCTCCTGTACAGCTTTTGGATTCACGTTTGAGGATTTTGGCA

TGCACTGGGTCCGTCAAGCTCCAGGGAAGGGTCTGGAGTGGGTCTCTCTT

GTTAGTGGGAAGGTGGTAGCAAATACTATGCCGACTCTGTGAAGGGCCG

GTTCACCATCTCCAGAGACAACAAGAAGCACTCCCTGTATCTGCACATGA

ACAGTCTGAAAACTGAGGACACCGCCTTGTATTACTGTGCAAAAGATGTA

TGGACCTACCACTATGATAGCAGTGGTTACCAATACTACTACGGTATGGA

CGTCTGGGGC

6A Heavy chain variable domain AA sequence,
SEQ ID NO: 4
EVQLVESGGGVVKPGGSLRLSCTAFGFTFEDFGMHWVRQAPGKGLEWVSL

VSGEGGSKYYADSVKGRFTISRDNKKHSLYLHMNSLKTEDTALYYCAKDV

WTYHYDSSGYQYYYGMDVW

6A Light chain DNA sequence,
SEQ ID NO: 5
TCAGGAGCCTGCTGTGTCTGTGGCCTTGGGACAGACAGTCAGGATCACAT
GCCAAGGAGACAGCCTCAGAAGCTACTCGGCAAGTTGGTACCAGCAGAGG
CCAGGACAGGCCCCTCTTTTTGTCATGTATGGTAAGGACAAGCGGCCCTC
AGGGATCCCAGACAGATTCTCTGGCTCCGCCTCAGGGAACACAGCTTCCT
TGACCATTACTGGGGCTCAGGCGGAAGATGAGGCTGACTATTACTGTAAC
TGCCGGGACAGCAGTAATCAATATTGGATTTTCGGCGGAGGGACCAAGGT
GACCGTCCTAGGTCAGCCCAAGGCTGCCCCCTCGGTCACTCTGTTCCCGC
CCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAG
CCCCGTCAAGGCGGGAGTGGAGACCACCACACCCTCCAAACAAAGCAACA
ACAAGTACGCGGCCAGCAGCTATCTGAGCCTGACGCCTGAGCAGTGGAAG
TCCCACAGAAGCTACAGCTGCC 6A Light chain AA sequence,
SEQ ID NO: 6
QEPAVSVALGQTVRITCQGDSLRSYSASWYQQRPGQAPLFVMYGKDKRPS
GIPDRFSGSASGNTASLTITGAQAEDEADYYCNCRDSSNQYWIFGGGTKV
TVLGQPKAAPSVTLFPPSSEELQANKATLVCLISDFYPGAVTVAWKADSS
PVKAGVETTTPSKQSNNKYAASSYLSLTPEQWKSHRSYSC 6A Light chain variable domain DNA sequence,
SEQ ID NO: 7
TCAGGAGCCTGCTGTGTCTGTGGCCTTGGGACAGACAGTCAGGATCACAT
GCCAAGGAGACAGCCTCAGAAGCTACTCGGCAAGTTGGTACCAGCAGAGG
CCAGGACAGGCCCCTCTTTTTGTCATGTATGGTAAGGACAAGCGGCCCTC
AGGGATCCCAGACAGATTCTCTGGCTCCGCCTCAGGGAACACAGCTTCCT
TGACCATTACTGGGGCTCAGGCGGAAGATGAGGCTGACTATTACTGTAAC
TGCCGGGACAGCAGTAATCAATATTGGATTTTC 6A Light chain variable domain AA sequence,
SEQ ID NO: 8
QEPAVSVALGQTVRITCQGDSLRSYSASWYQQRPGQAPLEVMYGKDKRPS
GIPDRFSGSASGNTASLTITGAQAEDEADYYCNCRDSSNQYWIF 6A scfv DNA sequence,
SEQ ID NO: 9
AGATCTTCTGAGCTGACTCAGGAGCCTGCTGTGTCTGTGGCCTTGGGACA
GACAGTCAGGATCACATGCCAAGGAGACAGCCTCAGAAGCTACTCGGCAA
GTTGGTACCAGCAGAGGCCAGGACAGGCCCCTCTTTTTGTCATGTATGGT
AAGGACAAGCGGCCCTCAGGGATCCCAGACAGATTCTCTGGCTCCGCCTC
AGGGAACACAGCTTCCTTGACCATTACTGGGGCTCAGGCGGAAGATGAGG
CTGACTATTACTGTAACTGCCGGGACAGCAGTAATCAATATTGGATTTTC
GGCGGAGGGACCAAGGTGACCGTCCTAGGTGGTGGTGGGGGGTCTGGAGG
AGGCTCGAGTGGCGGCGGTGGTTCGGGAGGCGGAGGCAGCGAAGTGCAAT
TGGTGGAGTCTGGGGGAGGCGTGGTGAAGCCGGGGGGGTCCCTGAGACTC
TCCTGTACAGCTTTTGGATTCACGTTTGAGGATTTTGGCATGCACTGGGT
CCGTCAAGCTCCAGGGAAGGGTCTGGAGTGGGTCTCTCTTGTTAGTGGGG
AAGGTGGTAGCAAATACTATGCCGACTCTGTGAAGGGCCGGTTCACCATC
TCCAGAGACAACAAGAAGCACTCCCTGTATCTGCACATGAACAGTCTGAA
AACTGAGGACACCGCCTTGTATTACTGTGCAAAAGATGTATGGACCTACC
ACTATGATAGCAGTGGTTACCAATACTACTACGGTATGGACGTCTGGGGC
CAAGGGACCACGGTCACCGTCTCCTGA 6A scfv AA sequence,
SEQ ID NO: 10
RSSELTQDPAVSVALGQTVRITCQGDSLRSYSASWYQQRPGQAPLFVMYG
KDKRPSGIPDRFSGSASGNTASLTITGAQAEDEADYYCNCRDSSNQYWIF
GGGTKVTVLGGGGSGGGSSGGGGSGGGGSEVQLVESGGGVVKPGGSLRL
SCTAFGFTFEDFGMHWVRQAPGKGLEWVSLVSGEGGSKYYADSVKGRFTI
SRDNKKHSLYLHMNSLKTEDTALYYCAKDVWTYHYDSSGYQYYYGMDVWG
QGTTVTVS The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of making a hybridoma, said method comprising culturing peripheral blood mononuclear cells (PBMCs) enriched for CD27+ PBMCs in the presence of CD40L and cytokines comprising IL-4 and IL-10 for a period of time in vitro, combining said cultured PBMCs enriched for CD27+ PBMCs with fusion partner cells, and fusing said cultured PBMCs enriched for CD27+ PBMCs with said fusion partner cells, whereby fusion of CD27+ B cells of said cultured PBMCs with said fusion partner cells produces monoclonal antibody-producing hybridomas.

2. The method of claim 1, wherein the concentration of IL-4 in the CD27+ enriched PBMC culture is about 2 ng/ml.

3. The method of claim 1, wherein the concentration of IL-10 in the CD27+ enriched PBMC culture is about 10 ng/ml.

4. The method of claim 1, wherein CD40L is provided in the form of CD40L displayed on the surface of tCD40L cells during the CD27+ enriched PBMC culturing.

5. The method of claim 1, wherein the fusion partner cells ectopically expresses mIL-6 and hTERT.

6. The method of claim 1, wherein said PBMSs enriched for CD27+ PBMCs are isolated from an immunized subject.

7. A method of producing a monoclonal antibody, the method comprising:
culturing peripheral blood mononuclear cells (PBMCs) enriched for CD27+ PBMCs in the presence of CD40L and cytokines comprising IL-4 and IL-10 for a period of time in vitro,
combining said cultured PBMCs enriched for CD27+ PBMCs with fusion partner cells,
fusing CD27+ B cells of said PBMCs enriched for CD27+ PBMCs with said fusion partner cells,
selecting a hybridoma that produces said monoclonal antibody, and
culturing said hybridoma to produce said monoclonal antibody.

8. The method of claim 7, wherein the concentration of IL-4 in the CD27+ enriched PBMC culture is about 2 ng/ml.

9. The method of claim 7, wherein the concentration of IL-10 in the CD27+ enriched PBMC culture is about 10 ng/ml.

10. The method of claim 7, wherein CD40L is provided in the form of CD40L displayed on the surface of tCD40L cells during the CD27+ enriched PBMC culturing.

11. The method of claim 7, wherein the fusion partner cells ectopically expresses mIL-6 and hTERT.

12. The method of claim 7, wherein said enriched for CD27+ PBMCs are isolated from an immunized subject.

13. A method of making a library of hybridomas, said method comprising
culturing PBMCs enriched for CD27+ PBMCs in the presence CD40L and cytokines comprising IL-4 and IL-10 for a period of time in vitro,
combining said cultured PBMCs enriched for CD27+ PBMCs with fusion partner cells, and
fusing said cultured PBMCs enriched for CD27+ PBMCs with said fusion partner cells, whereby fusion of CD27+ B cells of said cultured PBMCs with said fusion partner cells produces a library of monoclonal antibody-producing hybridomas from said CD27+ B cells and said fusion partner cells.

* * * * *